(12) United States Patent
Nakajima et al.

(10) Patent No.: US 8,268,794 B2
(45) Date of Patent: Sep. 18, 2012

(54) PHARMACEUTICAL CONTAINING HIF-1 ALPHA AND HIF-2 ALPHA EXPRESSION INHIBITOR

(75) Inventors: Takeshi Nakajima, Hyogo (JP); Emi Nakajima, Hyogo (JP); Mitsuyoshi Azuma, Hyogo (JP)

(73) Assignee: Senju Pharmaceutical Co., Ltd., Osaka-shi (JP)

( * ) Notice: Subject to any disclaimer, the term of this patent is extended or adjusted under 35 U.S.C. 154(b) by 119 days.

(21) Appl. No.: 12/672,473

(22) PCT Filed: Aug. 5, 2008

(86) PCT No.: PCT/JP2008/064038
§ 371 (c)(1),
(2), (4) Date: Mar. 3, 2010

(87) PCT Pub. No.: WO2009/020119
PCT Pub. Date: Feb. 12, 2009

(65) Prior Publication Data
US 2011/0213008 A1    Sep. 1, 2011

(30) Foreign Application Priority Data

Aug. 6, 2007 (JP) ................................. 2007-204585

(51) Int. Cl.
*A61K 48/00* (2006.01)
*C07H 21/02* (2006.01)
*C07H 21/04* (2006.01)
(52) U.S. Cl. .................... 514/44; 536/23.1; 536/24.5
(58) Field of Classification Search .................. None
See application file for complete search history.

(56) References Cited

U.S. PATENT DOCUMENTS 7,217,572 B2    5/2007  Ward et al.
2005/0163781 A1 *  7/2005  Koninckx et al. .......... 424/155.1

FOREIGN PATENT DOCUMENTS

| JP | 2006-504433 A | 2/2006 |
| WO | WO 2004/042024 A2 | 5/2004 |
| WO | WO 2006/050734 A2 | 5/2006 |
| WO | WO 2007/002718 A2 | 1/2007 |

OTHER PUBLICATIONS

Penfold et al. (Progress in Retinal and Eye Research, vol. 20, Issue 3, May 2001, pp. 385-414).*
Scherer et al. (Nat. Biotechnol., 2003, 21(12), pp. 1457-1465).*
Zhang et al. (Current Pharmaceutical Biotechnology 2004, vol. 5, p. 1-7).*
Ji et al., *Nanjing Yike Daxue Xuebao*, 26(5): 305-309 (2006).
Raval et al., *Molecular and Cellular Biology*, 25(13): 5675-5686 (2005).
Semenza, *Annu. Rev. Cell Dev. Biol.*, 15: 551-578 (1999).
Sowter et al., *Cancer Research*, 63: 6130-6134 (2003).
Warnecke et al., *FASEB Journal*, 12: 1462-1464 (2004).
Duxbury et al., *Annals of Surgery*, 240(4): 667-676 (2004).
Japanese Patent Office, International Search Report in International Patent Application No. PCT/JP2008/064038 (Sep. 16, 2008).
Forooghian et al., *Br. J. Ophthalmol.*, 91: 1406-1410 (2007).
Spilsbury et al., *American Journal of Pathology*, 157(1): 135-144 (2000).

* cited by examiner

*Primary Examiner* — Amy Bowman
(74) *Attorney, Agent, or Firm* — Leydig, Voit & Mayer, Ltd.

(57) ABSTRACT

Provided is a pharmaceutical product exhibiting a high therapeutic effect in the treatment of retinal diseases associated with angiogenesis such as age-related macular degeneration, diabetic retinopathy and the like. A therapeutic agent for a retinal disease, containing a substance specifically inhibiting HIF-1α expression and a substance specifically inhibiting HIF-2α expression. The aforementioned inhibitory substances, which are active ingredients in the therapeutic agent of the present invention, are nucleic acids capable of inducing RNAi, antisense nucleic acids or ribozymes for HIF-1α and HIF-2α, or expression vectors thereof.

6 Claims, 4 Drawing Sheets

Expression of HIF-1α in RPE cells

Expression of HIF-2α in RPE cells

SEQUENCE LISTING

<160> NUMBER OF SEQ ID NOS: 36

<210> SEQ ID NO 1
<211> LENGTH: 3958
<212> TYPE: DNA
<213> ORGANISM: Homo sapiens
<220> FEATURE:
<221> NAME/KEY: CDS
<222> LOCATION: (285)..(2765)

<400> SEQUENCE: 1

```
gtgctgcctc gtctgagggg acaggaggat caccctcttc gtcgcttcgg ccagtgtgtc      60
gggctgggcc ctgacaagcc acctgaggag aggctcggag ccgggccccgg accccggcga    120 ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240
ctgggggccg cccgccgtga agacatcgcg gggaccgatt cacc atg gag ggc gcc    296
                                                Met Glu Gly Ala
                                                  1 ggc ggc gcg aac gac aag aaa aag ata agt tct gaa cgt cga aaa gaa    344
Gly Gly Ala Asn Asp Lys Lys Lys Ile Ser Ser Glu Arg Arg Lys Glu
  5                  10                  15                  20 aag tct cga gat gca gcc aga tct cgg aga agt aaa gaa tct gaa gtt    392
Lys Ser Arg Asp Ala Ala Arg Ser Arg Arg Ser Lys Glu Ser Glu Val
                 25                  30                  35 ttt tat gag ctt gct cat cag ttg cca ctt cca cat aat gtg agt tcg    440
Phe Tyr Glu Leu Ala His Gln Leu Pro Leu Pro His Asn Val Ser Ser
             40                  45                  50 cat ctt gat aag gcc tct gtg atg agg ctt acc atc agc tat ttg cgt    488
His Leu Asp Lys Ala Ser Val Met Arg Leu Thr Ile Ser Tyr Leu Arg
         55                  60                  65 gtg agg aaa ctt ctg gat gct ggt gat ttg gat att gaa gat gac atg    536
Val Arg Lys Leu Leu Asp Ala Gly Asp Leu Asp Ile Glu Asp Asp Met
     70                  75                  80 aaa gca cag atg aat tgc ttt tat ttg aaa gcc ttg gat ggt ttt gtt    584
Lys Ala Gln Met Asn Cys Phe Tyr Leu Lys Ala Leu Asp Gly Phe Val
 85                  90                  95                 100 atg gtt ctc aca gat gat ggt gac atg att tac att tct gat aat gtg    632
Met Val Leu Thr Asp Asp Gly Asp Met Ile Tyr Ile Ser Asp Asn Val
                105                 110                 115 aac aaa tac atg gga tta act cag ttt gaa cta act gga cac agt gtg    680
Asn Lys Tyr Met Gly Leu Thr Gln Phe Glu Leu Thr Gly His Ser Val
            120                 125                 130 ttt gat ttt act cat cca tgt gac cat gag gaa atg aga gaa atg ctt    728
Phe Asp Phe Thr His Pro Cys Asp His Glu Glu Met Arg Glu Met Leu
        135                 140                 145 aca cac aga aat ggc ctt gtg aaa aag ggt aaa gaa caa aac aca cag    776
Thr His Arg Asn Gly Leu Val Lys Lys Gly Lys Glu Gln Asn Thr Gln
    150                 155                 160 cga agc ttt ttt ctc aga atg aag tgt acc cta act agc cga gga aga    824
Arg Ser Phe Phe Leu Arg Met Lys Cys Thr Leu Thr Ser Arg Gly Arg
165                 170                 175                 180 act atg aac ata aag tct gca aca tgg aag gta ttg cac tgc aca ggc    872
Thr Met Asn Ile Lys Ser Ala Thr Trp Lys Val Leu His Cys Thr Gly
                185                 190                 195 cac att cac gta tat gat acc aac agt aac caa cct cag tgt ggg tat    920
His Ile His Val Tyr Asp Thr Asn Ser Asn Gln Pro Gln Cys Gly Tyr
            200                 205                 210 aag aaa cca cct atg acc tgc ttg gtg ctg att tgt gaa ccc att cct    968
```

```
                                                              -continued

Lys Lys Pro Pro Met Thr Cys Leu Val Leu Ile Cys Glu Pro Ile Pro
        215                 220                 225 cac cca tca aat att gaa att cct tta gat agc aag act ttc ctc agt      1016
His Pro Ser Asn Ile Glu Ile Pro Leu Asp Ser Lys Thr Phe Leu Ser
230                 235                 240 cga cac agc ctg gat atg aaa ttt tct tat tgt gat gaa aga att acc      1064
Arg His Ser Leu Asp Met Lys Phe Ser Tyr Cys Asp Glu Arg Ile Thr
245                 250                 255                 260 gaa ttg atg gga tat gag cca gaa gaa ctt tta ggc cgc tca att tat      1112
Glu Leu Met Gly Tyr Glu Pro Glu Glu Leu Leu Gly Arg Ser Ile Tyr
                265                 270                 275 gaa tat tat cat gct ttg gac tct gat cat ctg acc aaa act cat cat      1160
Glu Tyr Tyr His Ala Leu Asp Ser Asp His Leu Thr Lys Thr His His
            280                 285                 290 gat atg ttt act aaa gga caa gtc acc aca gga cag tac agg atg ctt      1208
Asp Met Phe Thr Lys Gly Gln Val Thr Thr Gly Gln Tyr Arg Met Leu
        295                 300                 305 gcc aaa aga ggt gga tat gtc tgg gtt gaa act caa gca act gtc ata      1256
Ala Lys Arg Gly Gly Tyr Val Trp Val Glu Thr Gln Ala Thr Val Ile
310                 315                 320 tat aac acc aag aat tct caa cca cag tgc att gta tgt gtg aat tac      1304
Tyr Asn Thr Lys Asn Ser Gln Pro Gln Cys Ile Val Cys Val Asn Tyr
325                 330                 335                 340 gtt gtg agt ggt att att cag cac gac ttg att ttc tcc ctt caa caa      1352
Val Val Ser Gly Ile Ile Gln His Asp Leu Ile Phe Ser Leu Gln Gln
                345                 350                 355 aca gaa tgt gtc ctt aaa ccg gtt gaa tct tca gat atg aaa atg act      1400
Thr Glu Cys Val Leu Lys Pro Val Glu Ser Ser Asp Met Lys Met Thr
            360                 365                 370 cag cta ttc acc aaa gtt gaa tca gaa gat aca agt agc ctc ttt gac      1448
Gln Leu Phe Thr Lys Val Glu Ser Glu Asp Thr Ser Ser Leu Phe Asp
        375                 380                 385 aaa ctt aag aag gaa cct gat gct tta act ttg ctg gcc cca gcc gct      1496
Lys Leu Lys Lys Glu Pro Asp Ala Leu Thr Leu Leu Ala Pro Ala Ala
390                 395                 400 gga gac aca atc ata tct tta gat ttt ggc agc aac gac aca gaa act      1544
Gly Asp Thr Ile Ile Ser Leu Asp Phe Gly Ser Asn Asp Thr Glu Thr
405                 410                 415                 420 gat gac cag caa ctt gag gaa gta cca tta tat aat gat gta atg ctc      1592
Asp Asp Gln Gln Leu Glu Glu Val Pro Leu Tyr Asn Asp Val Met Leu
                425                 430                 435 ccc tca ccc aac gaa aaa tta cag aat ata aat ttg gca atg tct cca      1640
Pro Ser Pro Asn Glu Lys Leu Gln Asn Ile Asn Leu Ala Met Ser Pro
            440                 445                 450 tta ccc acc gct gaa acg cca aag cca ctt cga agt agt gct gac cct      1688
Leu Pro Thr Ala Glu Thr Pro Lys Pro Leu Arg Ser Ser Ala Asp Pro
        455                 460                 465 gca ctc aat caa gaa gtt gca tta aaa tta gaa cca aat cca gag tca      1736
Ala Leu Asn Gln Glu Val Ala Leu Lys Leu Glu Pro Asn Pro Glu Ser
470                 475                 480 ctg gaa ctt tct ttt acc atg ccc cag att cag gat cag aca cct agt      1784
Leu Glu Leu Ser Phe Thr Met Pro Gln Ile Gln Asp Gln Thr Pro Ser
485                 490                 495                 500 cct tcc gat gga agc act aga caa agt tca cct gag cct aat agt ccc      1832
Pro Ser Asp Gly Ser Thr Arg Gln Ser Ser Pro Glu Pro Asn Ser Pro
                505                 510                 515 agt gaa tat tgt ttt tat gtg gat agt gat atg gtc aat gaa ttc aag      1880
Ser Glu Tyr Cys Phe Tyr Val Asp Ser Asp Met Val Asn Glu Phe Lys
            520                 525                 530 ttg gaa ttg gta gaa aaa ctt ttt gct gaa gac aca gaa gca aag aac      1928
```

```
                Leu Glu Leu Val Glu Lys Leu Phe Ala Glu Asp Thr Glu Ala Lys Asn
                        535                 540                 545 cca ttt tct act cag gac aca gat tta gac ttg gag atg tta gct ccc        1976
Pro Phe Ser Thr Gln Asp Thr Asp Leu Asp Leu Glu Met Leu Ala Pro
550                 555                 560 tat atc cca atg gat gat gac ttc cag tta cgt tcc ttc gat cag ttg        2024
Tyr Ile Pro Met Asp Asp Asp Phe Gln Leu Arg Ser Phe Asp Gln Leu
565                 570                 575                 580 tca cca tta gaa agc agt tcc gca agc cct gaa agc gca agt cct caa        2072
Ser Pro Leu Glu Ser Ser Ser Ala Ser Pro Glu Ser Ala Ser Pro Gln
                585                 590                 595 agc aca gtt aca gta ttc cag cag act caa ata caa gaa cct act gct        2120
Ser Thr Val Thr Val Phe Gln Gln Thr Gln Ile Gln Glu Pro Thr Ala
                600                 605                 610 aat gcc acc act acc act gcc acc act gat gaa tta aaa aca gtg aca        2168
Asn Ala Thr Thr Thr Thr Ala Thr Thr Asp Glu Leu Lys Thr Val Thr
                615                 620                 625 aaa gac cgt atg gaa gac att aaa ata ttg att gca tct cca tct cct        2216
Lys Asp Arg Met Glu Asp Ile Lys Ile Leu Ile Ala Ser Pro Ser Pro
630                 635                 640 acc cac ata cat aaa gaa act act agt gcc aca tca tca cca tat aga        2264
Thr His Ile His Lys Glu Thr Thr Ser Ala Thr Ser Ser Pro Tyr Arg
645                 650                 655                 660 gat act caa agt cgg aca gcc tca cca aac aga gca gga aaa gga gtc        2312
Asp Thr Gln Ser Arg Thr Ala Ser Pro Asn Arg Ala Gly Lys Gly Val
                665                 670                 675 ata gaa cag aca gaa aaa tct cat cca aga agc cct aac gtg tta tct        2360
Ile Glu Gln Thr Glu Lys Ser His Pro Arg Ser Pro Asn Val Leu Ser
                680                 685                 690 gtc gct ttg agt caa aga act aca gtt cct gag gaa gaa cta aat cca        2408
Val Ala Leu Ser Gln Arg Thr Thr Val Pro Glu Glu Glu Leu Asn Pro
                695                 700                 705 aag ata cta gct ttg cag aat gct cag aga aag cga aaa atg gaa cat        2456
Lys Ile Leu Ala Leu Gln Asn Ala Gln Arg Lys Arg Lys Met Glu His
710                 715                 720 gat ggt tca ctt ttt caa gca gta gga att gga aca tta tta cag cag        2504
Asp Gly Ser Leu Phe Gln Ala Val Gly Ile Gly Thr Leu Leu Gln Gln
725                 730                 735                 740 cca gac gat cat gca gct act aca tca ctt tct tgg aaa cgt gta aaa        2552
Pro Asp Asp His Ala Ala Thr Thr Ser Leu Ser Trp Lys Arg Val Lys
                745                 750                 755 gga tgc aaa tct agt gaa cag aat gga atg gag caa aag aca att att        2600
Gly Cys Lys Ser Ser Glu Gln Asn Gly Met Glu Gln Lys Thr Ile Ile
                760                 765                 770 tta ata ccc tct gat tta gca tgt aga ctg ctg ggg caa tca atg gat        2648
Leu Ile Pro Ser Asp Leu Ala Cys Arg Leu Leu Gly Gln Ser Met Asp
                775                 780                 785 gaa agt gga tta cca cag ctg acc agt tat gat tgt gaa gtt aat gct        2696
Glu Ser Gly Leu Pro Gln Leu Thr Ser Tyr Asp Cys Glu Val Asn Ala
790                 795                 800 cct ata caa ggc agc aga aac cta ctg cag ggt gaa gaa tta ctc aga        2744
Pro Ile Gln Gly Ser Arg Asn Leu Leu Gln Gly Glu Glu Leu Leu Arg
805                 810                 815                 820 gct ttg gat caa gtt aac tga gcttttttctt aatttcattc ctttttttgg         2795
Ala Leu Asp Gln Val Asn
                825 acactggtgg ctcactacct aaagcagtct atttatattt tctacatcta attttagaag     2855 cctggctaca atactgcaca aacttggtta gttcaatttt tgatccccct tctacttaat     2915 ttacattaat gctcttttt agtatgttct ttaatgctgg atcacagaca gctcatttc       2975
```

-continued

```
tcagttttttt ggtatttaaaa ccattgcatt gcagtagcat cattttaaaa aatgcaccct    3035
tttatttatt tattttggc tagggagttt atccctttt cgaattattt ttaagaagat       3095
gccaatataa tttttgtaag aaggcagtaa cctttcatca tgatcatagg cagttgaaaa     3155 attttacac ctttttttc acattttaca taaataataa tgctttgcca gcagtacgtg       3215
gtagccacaa ttgcacaata tattttctta aaaatacca gcagttactc atggaatata     3275
ttctgcgttt ataaaactag ttttaagaa gaaattttt ttggcctatg aaattgttaa       3335
acctggaaca tgacattgtt aatcatataa taatgattct taaatgctgt atggtttatt    3395
atttaaatgg gtaaagccat ttacataata tagaaagata tgcatatatc tagaaggtat    3455
gtggcattta tttggataaa attctcaatt cagagaaatc atctgatgtt tctatagtca    3515
ctttgccagc tcaaaagaaa acaatacccct atgtagttgt ggaagtttat gctaatattg   3575
tgtaactgat attaaaccta aatgttctgc ctaccctgtt ggtataaaga tattttgagc    3635
agactgtaaa caagaaaaaa aaatcatgc attcttagca aaattgccta gtatgttaat     3695
ttgctcaaaa tacaatgttt gattttatgc actttgtcgc tattaacatc ctttttttca    3755
tgtagatttc aataattgag taattttaga agcattattt taggaatata tagttgtcac    3815
agtaaatatc ttgttttttc tatgtacatt gtacaaattt ttcattcctt ttgctctttg    3875
tggttggatc taacactaac tgtattgttt tgttacatca aataaacatc ttctgtggac    3935
caggaaaaaa aaaaaaaaaa aaa                                            3958
```

<210> SEQ ID NO 2
<211> LENGTH: 826
<212> TYPE: PRT
<213> ORGANISM: Homo sapiens

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro

```
                195                 200                 205
Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620
```

```
Lys Thr Val Thr Lys Asp Arg Met Glu Asp Ile Lys Ile Leu Ile Ala
625                 630                 635                 640

Ser Pro Ser Pro Thr His Ile His Lys Glu Thr Ser Ala Thr Ser
            645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 3
<211> LENGTH: 5186
<212> TYPE: DNA
<213> ORGANISM: Homo sapiens
<220> FEATURE:
<221> NAME/KEY: CDS
<222> LOCATION: (489)..(3101)

<400> SEQUENCE: 3
gccacacggg tccggtgccc gctgcgcttc cgccccagcg ctcctgaggc ggccgtacaa      60
tcctcggcag tgtcctgaga ctgtatggtc agctcagccc ggcctccgac tccttccgac     120
tcccagcatt cgagccactt ttttttttct ttgaaaactc agaaaagtga ctccttttcc     180
agggaaaaag gaacttgggt tcccttctct ccgtcctctt ttcgggtctg acagcctcca     240
cccactcctt ccccggaccc cgcctccgcg cgcaggttcc tcccagtcac ctttctccac     300
ccccgccccc gcacctagcc cgccgcgcgc accttccac  ctgactgcgc ggggcgctcg     360
ggacctgcgc gcacctcgga ccttcaccac ccgcccgggc cgcggggagc ggacgagggc     420
cacagccccc cacccgccag ggagcccagg tgctcggcgt ctgaacgtct caaagggcca     480 cagcgaca atg aca gct gac aag gag aag aaa agg agt agc tcg gag agg    530
         Met Thr Ala Asp Lys Glu Lys Lys Arg Ser Ser Ser Glu Arg
         1               5                   10 agg aag gag aag tcc cgg gat gct gcg cgg tgc cgg cgg agc aag gag    578
Arg Lys Glu Lys Ser Arg Asp Ala Ala Arg Cys Arg Arg Ser Lys Glu
15              20                  25                  30 acg gag gtg ttc tat gag ctg gcc cat gag ctg cct ctg ccc cac agt    626
Thr Glu Val Phe Tyr Glu Leu Ala His Glu Leu Pro Leu Pro His Ser
                35                  40                  45 gtg agc tcc cat ctg gac aag gcc tcc atc atg cga ctg gca atc agc    674
Val Ser Ser His Leu Asp Lys Ala Ser Ile Met Arg Leu Ala Ile Ser
```

-continued

```
                    50                      55                      60
ttc ctg cga aca cac aag ctc ctc tcc tca gtt tgc tct gaa aac gag      722
Phe Leu Arg Thr His Lys Leu Leu Ser Ser Val Cys Ser Glu Asn Glu
         65                      70                      75 tcc gaa gcc gaa gct gac cag cag atg gac aac ttg tac ctg aaa gcc      770
Ser Glu Ala Glu Ala Asp Gln Gln Met Asp Asn Leu Tyr Leu Lys Ala
     80                      85                      90 ttg gag ggt ttc att gcc gtg gtg acc caa gat ggc gac atg atc ttt      818
Leu Glu Gly Phe Ile Ala Val Val Thr Gln Asp Gly Asp Met Ile Phe
 95                     100                     105                     110 ctg tca gaa aac atc agc aag ttc atg gga ctt aca cag gtg gag cta      866
Leu Ser Glu Asn Ile Ser Lys Phe Met Gly Leu Thr Gln Val Glu Leu
                    115                     120                     125 aca gga cat agt atc ttt gac ttc act cat ccc tgc gac cat gag gag      914
Thr Gly His Ser Ile Phe Asp Phe Thr His Pro Cys Asp His Glu Glu
                130                     135                     140 att cgt gag aac ctg agt ctc aaa aat ggc tct ggt ttt ggg aaa aaa      962
Ile Arg Glu Asn Leu Ser Leu Lys Asn Gly Ser Gly Phe Gly Lys Lys
            145                     150                     155 agc aaa gac atg tcc aca gag cgg gac ttc ttc atg agg atg aag tgc     1010
Ser Lys Asp Met Ser Thr Glu Arg Asp Phe Phe Met Arg Met Lys Cys
        160                     165                     170 acg gtc acc aac aga ggc cgt act gtc aac ctc aag tca gcc acc tgg     1058
Thr Val Thr Asn Arg Gly Arg Thr Val Asn Leu Lys Ser Ala Thr Trp
175                     180                     185                     190 aag gtc ttg cac tgc acg ggc cag gtg aaa gtc tac aac aac tgc cct     1106
Lys Val Leu His Cys Thr Gly Gln Val Lys Val Tyr Asn Asn Cys Pro
                    195                     200                     205 cct cac aat agt ctg tgt ggc tac aag gag ccc ctg ctg tcc tgc ctc     1154
Pro His Asn Ser Leu Cys Gly Tyr Lys Glu Pro Leu Leu Ser Cys Leu
                210                     215                     220 atc atc atg tgt gaa cca atc cag cac cca tcc cac atg gac atc ccc     1202
Ile Ile Met Cys Glu Pro Ile Gln His Pro Ser His Met Asp Ile Pro
            225                     230                     235 ctg gat agc aag acc ttc ctg agc cgc cac agc atg gac atg aag ttc     1250
Leu Asp Ser Lys Thr Phe Leu Ser Arg His Ser Met Asp Met Lys Phe
        240                     245                     250 acc tac tgt gat gac aga atc aca gaa ctg att ggt tac cac cct gag     1298
Thr Tyr Cys Asp Asp Arg Ile Thr Glu Leu Ile Gly Tyr His Pro Glu
255                     260                     265                     270 gag ctg ctt ggc cgc tca gcc tat gaa ttc tac cat gcg cta gac tcc     1346
Glu Leu Leu Gly Arg Ser Ala Tyr Glu Phe Tyr His Ala Leu Asp Ser
                    275                     280                     285 gag aac atg acc aag agt cac cag aac ttg tgc acc aag ggt cag gta     1394
Glu Asn Met Thr Lys Ser His Gln Asn Leu Cys Thr Lys Gly Gln Val
                290                     295                     300 gta agt ggc cag tac cgg atg ctc gca aag cat ggg ggc tac gtg tgg     1442
Val Ser Gly Gln Tyr Arg Met Leu Ala Lys His Gly Gly Tyr Val Trp
            305                     310                     315 ctg gag acc cag ggg acg gtc atc tac aac cct cgc aac ctg cag ccc     1490
Leu Glu Thr Gln Gly Thr Val Ile Tyr Asn Pro Arg Asn Leu Gln Pro
        320                     325                     330 cag tgc atc atg tgt gtc aac tac gtc ctg agt gag att gag aag aat     1538
Gln Cys Ile Met Cys Val Asn Tyr Val Leu Ser Glu Ile Glu Lys Asn
335                     340                     345                     350 gac gtg gtg ttc tcc atg gac cag act gaa tcc ctg ttc aag ccc cac     1586
Asp Val Val Phe Ser Met Asp Gln Thr Glu Ser Leu Phe Lys Pro His
                    355                     360                     365 ctg atg gcc atg aac agc atc ttt gat agc agt ggc aag ggg gct gtg     1634
Leu Met Ala Met Asn Ser Ile Phe Asp Ser Ser Gly Lys Gly Ala Val
```

-continued

|     |     |     | 370 |     |     |     | 375 |     |     |     | 380 |     |     |     |      |
| --- | --- | --- | --- | --- | --- | --- | --- | --- | --- | --- | --- | --- | --- | --- | ---- |
| tct | gag | aag | agt | aac | ttc | cta | ttc | acc | aag | cta | aag | gag | gag | ccc | gag  | 1682 |
| Ser | Glu | Lys | Ser | Asn | Phe | Leu | Phe | Thr | Lys | Leu | Lys | Glu | Glu | Pro | Glu  |
|     |     | 385 |     |     |     |     | 390 |     |     |     |     | 395 |     |     |      |

| gag | ctg | gcc | cag | ctg | gct | ccc | acc | cca | gga | gac | gcc | atc | atc | tct | ctg | 1730 |
| Glu | Leu | Ala | Gln | Leu | Ala | Pro | Thr | Pro | Gly | Asp | Ala | Ile | Ile | Ser | Leu |
| 400 |     |     |     |     | 405 |     |     |     |     | 410 |     |     |     |     |     |

| gat | ttc | ggg | aat | cag | aac | ttc | gag | gag | tcc | tca | gcc | tat | ggc | aag | gcc | 1778 |
| Asp | Phe | Gly | Asn | Gln | Asn | Phe | Glu | Glu | Ser | Ser | Ala | Tyr | Gly | Lys | Ala |
| 415 |     |     |     |     | 420 |     |     |     |     | 425 |     |     |     |     | 430 |

| atc | ctg | ccc | ccg | agc | cag | cca | tgg | gcc | acg | gag | ttg | agg | agc | cac | agc | 1826 |
| Ile | Leu | Pro | Pro | Ser | Gln | Pro | Trp | Ala | Thr | Glu | Leu | Arg | Ser | His | Ser |
|     |     |     |     | 435 |     |     |     |     | 440 |     |     |     |     | 445 |     |

| acc | cag | agc | gag | gct | ggg | agc | ctg | cct | gcc | ttc | acc | gtg | ccc | cag | gca | 1874 |
| Thr | Gln | Ser | Glu | Ala | Gly | Ser | Leu | Pro | Ala | Phe | Thr | Val | Pro | Gln | Ala |
|     |     |     | 450 |     |     |     |     | 455 |     |     |     |     | 460 |     |     |

| gct | gcc | ccg | ggc | agc | acc | acc | ccc | agt | gcc | acc | agc | agc | agc | agc | 1922 |
| Ala | Ala | Pro | Gly | Ser | Thr | Thr | Pro | Ser | Ala | Thr | Ser | Ser | Ser | Ser |
|     | 465 |     |     |     |     | 470 |     |     |     |     | 475 |     |     |     |

| tgc | tcc | acg | ccc | aat | agc | cct | gaa | gac | tat | tac | aca | tct | ttg | gat | aac | 1970 |
| Cys | Ser | Thr | Pro | Asn | Ser | Pro | Glu | Asp | Tyr | Tyr | Thr | Ser | Leu | Asp | Asn |
|     | 480 |     |     |     |     | 485 |     |     |     |     | 490 |     |     |     |     |

| gac | ctg | aag | att | gaa | gtg | att | gag | aag | ctc | ttc | gcc | atg | gac | aca | gag | 2018 |
| Asp | Leu | Lys | Ile | Glu | Val | Ile | Glu | Lys | Leu | Phe | Ala | Met | Asp | Thr | Glu |
| 495 |     |     |     |     | 500 |     |     |     |     | 505 |     |     |     |     | 510 |

| gcc | aag | gac | caa | tgc | agt | acc | cag | acg | gat | ttc | aat | gag | ctg | gac | ttg | 2066 |
| Ala | Lys | Asp | Gln | Cys | Ser | Thr | Gln | Thr | Asp | Phe | Asn | Glu | Leu | Asp | Leu |
|     |     |     |     | 515 |     |     |     |     | 520 |     |     |     |     | 525 |     |

| gag | aca | ctg | gca | ccc | tat | atc | ccc | atg | gac | ggg | gaa | gac | ttc | cag | cta | 2114 |
| Glu | Thr | Leu | Ala | Pro | Tyr | Ile | Pro | Met | Asp | Gly | Glu | Asp | Phe | Gln | Leu |
|     |     |     | 530 |     |     |     |     | 535 |     |     |     |     | 540 |     |     |

| agc | ccc | atc | tgc | ccc | gag | gag | cgg | ctc | ttg | gcg | gag | aac | cca | cag | tcc | 2162 |
| Ser | Pro | Ile | Cys | Pro | Glu | Glu | Arg | Leu | Leu | Ala | Glu | Asn | Pro | Gln | Ser |
|     |     | 545 |     |     |     |     | 550 |     |     |     |     | 555 |     |     |     |

| acc | ccc | cag | cac | tgc | ttc | agt | gcc | atg | aca | aac | atc | ttc | cag | cca | ctg | 2210 |
| Thr | Pro | Gln | His | Cys | Phe | Ser | Ala | Met | Thr | Asn | Ile | Phe | Gln | Pro | Leu |
|     | 560 |     |     |     |     | 565 |     |     |     |     | 570 |     |     |     |     |

| gcc | cct | gta | gcc | ccg | cac | agt | ccc | ttc | ctc | ctg | gac | aag | ttt | cag | cag | 2258 |
| Ala | Pro | Val | Ala | Pro | His | Ser | Pro | Phe | Leu | Leu | Asp | Lys | Phe | Gln | Gln |
| 575 |     |     |     |     | 580 |     |     |     |     | 585 |     |     |     |     | 590 |

| cag | ctg | gag | agc | aag | aag | aca | gag | ccc | gag | cac | cgg | ccc | atg | tcc | tcc | 2306 |
| Gln | Leu | Glu | Ser | Lys | Lys | Thr | Glu | Pro | Glu | His | Arg | Pro | Met | Ser | Ser |
|     |     |     |     | 595 |     |     |     |     | 600 |     |     |     |     | 605 |     |

| atc | ttc | ttt | gat | gcc | gga | agc | aaa | gca | tcc | ctg | cca | ccg | tgc | tgt | ggc | 2354 |
| Ile | Phe | Phe | Asp | Ala | Gly | Ser | Lys | Ala | Ser | Leu | Pro | Pro | Cys | Cys | Gly |
|     |     |     | 610 |     |     |     |     | 615 |     |     |     |     | 620 |     |     |

| cag | gcc | agc | acc | cct | ctc | tct | tcc | atg | ggg | ggc | aga | tcc | aat | acc | cag | 2402 |
| Gln | Ala | Ser | Thr | Pro | Leu | Ser | Ser | Met | Gly | Gly | Arg | Ser | Asn | Thr | Gln |
|     |     | 625 |     |     |     |     | 630 |     |     |     |     | 635 |     |     |     |

| tgg | ccc | cca | gat | cca | cca | tta | cat | ttt | ggg | ccc | aca | aag | tgg | gcc | gtc | 2450 |
| Trp | Pro | Pro | Asp | Pro | Pro | Leu | His | Phe | Gly | Pro | Thr | Lys | Trp | Ala | Val |
|     | 640 |     |     |     |     | 645 |     |     |     |     | 650 |     |     |     |     |

| ggg | gat | cag | cgc | aca | gag | ttc | ttg | gga | gca | gcg | ccg | ttg | ggg | ccc | cct | 2498 |
| Gly | Asp | Gln | Arg | Thr | Glu | Phe | Leu | Gly | Ala | Ala | Pro | Leu | Gly | Pro | Pro |
| 655 |     |     |     |     | 660 |     |     |     |     | 665 |     |     |     |     | 670 |

| gtc | tct | cca | ccc | cat | gtc | tcc | acc | ttc | aag | aca | agg | tct | gca | aag | ggt | 2546 |
| Val | Ser | Pro | Pro | His | Val | Ser | Thr | Phe | Lys | Thr | Arg | Ser | Ala | Lys | Gly |
|     |     |     |     | 675 |     |     |     |     | 680 |     |     |     |     | 685 |     |

| ttt | ggg | gct | cga | ggc | cca | gac | gtg | ctg | agt | ccg | gcc | atg | gta | gcc | ctc | 2594 |
| Phe | Gly | Ala | Arg | Gly | Pro | Asp | Val | Leu | Ser | Pro | Ala | Met | Val | Ala | Leu |

-continued

```
                   690             695             700
tcc aac aag ctg aag ctg aag cga cag ctg gag tat gaa gag caa gcc    2642
Ser Asn Lys Leu Lys Leu Lys Arg Gln Leu Glu Tyr Glu Glu Gln Ala
        705                 710                 715 ttc cag gac ctg agc ggg ggg gac cca cct ggt ggc agc acc tca cat    2690
Phe Gln Asp Leu Ser Gly Gly Asp Pro Pro Gly Gly Ser Thr Ser His
    720                 725                 730 ttg atg tgg aaa cgg atg aag aac ctc agg ggt ggg agc tgc cct ttg    2738
Leu Met Trp Lys Arg Met Lys Asn Leu Arg Gly Gly Ser Cys Pro Leu
735                 740                 745                 750 atg ccg gac aag cca ctg agc gca aat gta ccc aat gat aag ttc acc    2786
Met Pro Asp Lys Pro Leu Ser Ala Asn Val Pro Asn Asp Lys Phe Thr
            755                 760                 765 caa aac ccc atg agg ggc ctg ggc cat ccc ctg aga cat ctg ccg ctg    2834
Gln Asn Pro Met Arg Gly Leu Gly His Pro Leu Arg His Leu Pro Leu
        770                 775                 780 cca cag cct cca tct gcc atc agt ccc ggg gag aac agc aag agc agg    2882
Pro Gln Pro Pro Ser Ala Ile Ser Pro Gly Glu Asn Ser Lys Ser Arg
    785                 790                 795 ttc ccc cca cag tgc tac gcc acc cag tac cag gac tac agc ctg tcg    2930
Phe Pro Pro Gln Cys Tyr Ala Thr Gln Tyr Gln Asp Tyr Ser Leu Ser
800                 805                 810 tca gcc cac aag gtg tca ggc atg gca agc cgg ctg ctc ggg ccc tca    2978
Ser Ala His Lys Val Ser Gly Met Ala Ser Arg Leu Leu Gly Pro Ser
815                 820                 825                 830 ttt gag tcc tac ctg ctg ccc gaa ctg acc aga tat gac tgt gag gtg    3026
Phe Glu Ser Tyr Leu Leu Pro Glu Leu Thr Arg Tyr Asp Cys Glu Val
            835                 840                 845 aac gtg ccc gtg ctg gga agc tcc acg ctc ctg caa gga ggg gac ctc    3074
Asn Val Pro Val Leu Gly Ser Ser Thr Leu Leu Gln Gly Gly Asp Leu
        850                 855                 860 ctc aga gcc ctg gac cag gcc acc tga gccaggcctt ctacctgggc          3121
Leu Arg Ala Leu Asp Gln Ala Thr
    865                 870 agcacctctg ccgacgccgt cccaccagct tcactctctc cgtctgtttt tgcaactagg  3181
tatttctaac gccagcacac tatttacaag atggacttac ctggcagact tgcccaggtc  3241
accaagcagt ggccttttc tgagatgctc actttattat ccctattttt aaagtacaca  3301
attgttttac ctgttctgaa atgttcttaa attttgtagg attttttcc tccccacctt   3361
caatgacttc taatttatat tatccatagg tttctctccc tccttctcct tctcacacac  3421
aactgtccat actaacaagt ttggtgcatg tctgttcttc tgtagggaga agctttagct  3481
tcatttact aaaaagattc ctcgttattg ttgttgccaa agagaaacaa aaatgatttt   3541
gctttccaag cttggtttgt ggcgtctccc tcgcagagcc cttctcgttt cttttttaaa  3601
ctaatcacca tattgtaaat ttcagggttt ttttttttt gtttaagctg actctttgct   3661
ctaattttgg aaaaaagaa atgtgaaggg tcaactccaa cgtatgtggt tatctgtgaa   3721
agttgcacag cgtggctttt cctaaactgg tgttttccc ccgcatttgg tggatttttt   3781
attattattc aaaaacataa ctgagttttt taaaagagga gaaatttat atctgggtta   3841
agtgtttatc atatatatgg gtactttgta atatctaaaa acttagaaac ggaaatggaa  3901
tcctgctcac aaaatcactt taagatcttt tcgaagctgt taattttct tagtgttgtg   3961
gacactgcag acttgtccag tgctcccacg gcctgtacgg acactgtgga aggcctccct  4021
ctgtcggctt tttgccatct gtgatatgcc ataggtgtga caatccgagc agtggagtca  4081
ttcagcggga gcactgcgcg ctatcccctc acattctcta tgtactatgt atgtatgtat  4141
```

```
tattattatt gctgccaaga gggtctgatg gcacgttgtg gggtcggggg gtggggcggg      4201
gaagtgctct aacttttctt aaggttttgt tgctagccct tcaagtgcac tgagctatgt      4261
gactcggatg gtctttcaca cggcacattt ggacatttcc agaactacca tgagatggtt      4321
tagacgggaa ttcatgcaaa tgaggggtca aaaatggtat agtgaccccg tccacgtcct      4381
ccaagctcac gaccttggag ccccgtggag ctggactgag gaggaggctg cacagcggga      4441
gagcagctgg tccagaccag ccctgcagcc cccactcagc cggcagccag atggcccgc       4501 aaggcctcca gggatggccc ctagccacag gccctggctg aggtctctgg gtcggtcagt      4561
gacatgtagg taggaagcac tgaaaatagt gttcccagag cactttgcaa ctccctgggt      4621
aagagggacg acacctctgg tttttcaata ccaattacat ggaacttttc tgtaatgggt      4681
acaatgaaga agtttctaaa aacacacaca aagcacattg gccaactat ttagtaagcc       4741 cggatagact tattgccaaa acaaaaaat agctttcaaa agaaatttaa gttctatgag       4801
aaattcctta gtcatggtgt tgcgtaaatc atattttagc tgcacggcat taccccacac      4861
agggtggcag aacttgaagg gttactgacg tgtaaatgct ggtatttgat ttcctgtgtg      4921
tgttgccctg gcattaaggg cattttaccc ttgcagtttt actaaaacac tgaaaaatat      4981
tccaagcttc atattaaccc tacctgtcaa cgtaacgatt tcatgaacgt tattatattg      5041
tcgaattcct actgacaaca ttataactgt atgggagctt aactttataa ggaaatgtat      5101
tttgacactg gtatcttatt aaagtattct gatcctaaaa aaaaaaaaa aaaaaaaaaa       5161 aaaaaaaaaa aaaaaaaaaa aaaaa                                            5186

<210> SEQ ID NO 4
<211> LENGTH: 870
<212> TYPE: PRT
<213> ORGANISM: Homo sapiens

<400> SEQUENCE: 4

Met Thr Ala Asp Lys Glu Lys Lys Arg Ser Ser Glu Arg Arg Lys
1               5                   10                  15

Glu Lys Ser Arg Asp Ala Ala Arg Cys Arg Arg Ser Lys Glu Thr Glu
                20                  25                  30

Val Phe Tyr Glu Leu Ala His Glu Leu Pro Leu Pro His Ser Val Ser
            35                  40                  45

Ser His Leu Asp Lys Ala Ser Ile Met Arg Leu Ala Ile Ser Phe Leu
        50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
        115                 120                 125

His Ser Ile Phe Asp Phe Thr His Pro Cys Asp His Glu Glu Ile Arg
    130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175

Thr Asn Arg Gly Arg Thr Val Asn Leu Lys Ser Ala Thr Trp Lys Val
            180                 185                 190
```

-continued

```
Leu His Cys Thr Gly Gln Val Lys Val Tyr Asn Asn Cys Pro Pro His
        195                 200                 205
Asn Ser Leu Cys Gly Tyr Lys Glu Pro Leu Leu Ser Cys Leu Ile Ile
    210                 215                 220
Met Cys Glu Pro Ile Gln His Pro Ser His Met Asp Ile Pro Leu Asp
225                 230                 235                 240
Ser Lys Thr Phe Leu Ser Arg His Ser Met Asp Met Lys Phe Thr Tyr
                245                 250                 255
Cys Asp Asp Arg Ile Thr Glu Leu Ile Gly Tyr His Pro Glu Glu Leu
                260                 265                 270
Leu Gly Arg Ser Ala Tyr Glu Phe Tyr His Ala Leu Asp Ser Glu Asn
            275                 280                 285
Met Thr Lys Ser His Gln Asn Leu Cys Thr Lys Gly Gln Val Val Ser
    290                 295                 300
Gly Gln Tyr Arg Met Leu Ala Lys His Gly Gly Tyr Val Trp Leu Glu
305                 310                 315                 320
Thr Gln Gly Thr Val Ile Tyr Asn Pro Arg Asn Leu Gln Pro Gln Cys
                325                 330                 335
Ile Met Cys Val Asn Tyr Val Leu Ser Glu Ile Glu Lys Asn Asp Val
            340                 345                 350
Val Phe Ser Met Asp Gln Thr Glu Ser Leu Phe Lys Pro His Leu Met
    355                 360                 365
Ala Met Asn Ser Ile Phe Asp Ser Ser Gly Lys Gly Ala Val Ser Glu
370                 375                 380
Lys Ser Asn Phe Leu Phe Thr Lys Leu Lys Glu Glu Pro Glu Glu Leu
385                 390                 395                 400
Ala Gln Leu Ala Pro Thr Pro Gly Asp Ala Ile Ile Ser Leu Asp Phe
                405                 410                 415
Gly Asn Gln Asn Phe Glu Glu Ser Ser Ala Tyr Gly Lys Ala Ile Leu
            420                 425                 430
Pro Pro Ser Gln Pro Trp Ala Thr Glu Leu Arg Ser His Ser Thr Gln
    435                 440                 445
Ser Glu Ala Gly Ser Leu Pro Ala Phe Thr Val Pro Gln Ala Ala Ala
450                 455                 460
Pro Gly Ser Thr Thr Pro Ser Ala Thr Ser Ser Ser Ser Cys Ser
465                 470                 475                 480
Thr Pro Asn Ser Pro Glu Asp Tyr Tyr Thr Ser Leu Asp Asn Asp Leu
                485                 490                 495
Lys Ile Glu Val Ile Glu Lys Leu Phe Ala Met Asp Thr Glu Ala Lys
            500                 505                 510
Asp Gln Cys Ser Thr Gln Thr Asp Phe Asn Glu Leu Asp Leu Glu Thr
    515                 520                 525
Leu Ala Pro Tyr Ile Pro Met Asp Gly Glu Asp Phe Gln Leu Ser Pro
530                 535                 540
Ile Cys Pro Glu Glu Arg Leu Leu Ala Glu Asn Pro Gln Ser Thr Pro
545                 550                 555                 560
Gln His Cys Phe Ser Ala Met Thr Asn Ile Phe Gln Pro Leu Ala Pro
                565                 570                 575
Val Ala Pro His Ser Pro Phe Leu Leu Asp Lys Phe Gln Gln Gln Leu
            580                 585                 590
Glu Ser Lys Lys Thr Glu Pro Glu His Arg Pro Met Ser Ser Ile Phe
    595                 600                 605
Phe Asp Ala Gly Ser Lys Ala Ser Leu Pro Pro Cys Cys Gly Gln Ala
610                 615                 620
```

-continued

```
Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
            645                 650                 655

Gln Arg Thr Glu Phe Leu Gly Ala Ala Pro Leu Gly Pro Pro Val Ser
        660                 665                 670

Pro Pro His Val Ser Thr Phe Lys Thr Arg Ser Ala Lys Gly Phe Gly
    675                 680                 685

Ala Arg Gly Pro Asp Val Leu Ser Pro Ala Met Val Ala Leu Ser Asn
690                 695                 700

Lys Leu Lys Leu Lys Arg Gln Leu Glu Tyr Glu Glu Gln Ala Phe Gln
705                 710                 715                 720

Asp Leu Ser Gly Gly Asp Pro Pro Gly Gly Ser Thr Ser His Leu Met
                725                 730                 735

Trp Lys Arg Met Lys Asn Leu Arg Gly Gly Ser Cys Pro Leu Met Pro
            740                 745                 750

Asp Lys Pro Leu Ser Ala Asn Val Pro Asn Asp Lys Phe Thr Gln Asn
        755                 760                 765

Pro Met Arg Gly Leu Gly His Pro Leu Arg His Leu Pro Leu Pro Gln
    770                 775                 780

Pro Pro Ser Ala Ile Ser Pro Gly Glu Asn Ser Lys Ser Arg Phe Pro
785                 790                 795                 800

Pro Gln Cys Tyr Ala Thr Gln Tyr Gln Asp Tyr Ser Leu Ser Ser Ala
                805                 810                 815

His Lys Val Ser Gly Met Ala Ser Arg Leu Leu Gly Pro Ser Phe Glu
            820                 825                 830

Ser Tyr Leu Leu Pro Glu Leu Thr Arg Tyr Asp Cys Glu Val Asn Val
        835                 840                 845

Pro Val Leu Gly Ser Ser Thr Leu Leu Gln Gly Gly Asp Leu Leu Arg
    850                 855                 860

Ala Leu Asp Gln Ala Thr
865                 870

<210> SEQ ID NO 5
<211> LENGTH: 21
<212> TYPE: DNA
<213> ORGANISM: Artificial Sequence
<220> FEATURE:
<223> OTHER INFORMATION: Synthetic sense strand of siRNA for human HIF-1
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 5
ggaaccugau gcuuuaacun n                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic sense strand of siRNA for human HIF-1
      alpha
<220> FEATURE:
<223> OTHER INFORMATION: Combined DNA/RNA
<220> FEATURE:
<221> NAME/KEY: misc_feature
```

```
<222> LOCATION: (20)..(21)
<223> OTHER INFORMATION: n = deoxythymidine

<400> SEQUENCE: 6
ggguaaagaa caaaacacan n                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic sense strand of siRNA for human HIF-1
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 7
ggcagcagaa accuacugcn n                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic sense strand of siRNA for human HIF-1
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 8
gcacgacuug auuuucuccn n                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic sense strand of siRNA for human HIF-2
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 9
cggagguguu cuaugagcun n                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic sense strand of siRNA for human HIF-2
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 10
```
gguuuuguug cuagcccuun n                                               21

<210> SEQ ID NO 11
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-1 alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 11
aguuaaagca ucagguuccn n                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-1 alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 12
uguguuuugu ucuuuacccn n                                               21

<210> SEQ ID NO 13
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-1 alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 13
gcaguagguu ucugcugccn n                                               21

<210> SEQ ID NO 14
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-1 alpha
<220> FEATURE:
<223> OTHER INFORMATION: Combined DNA/RNA
<220> FEATURE:
<221> NAME/KEY: misc_feature
<222> LOCATION: (20)..(20)
<223> OTHER INFORMATION: n = deoxythymidine
<220> FEATURE:
<221> NAME/KEY: misc_feature
<222> LOCATION: (21)..(21)
<223> OTHER INFORMATION: n = deoxyguanosine

<400> SEQUENCE: 14

```
ggagaaaauc aagucgugcn n                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-2 alpha
<220> FEATURE:
<223> OTHER INFORMATION: Combined DNA/RNA
<220> FEATURE:
<221> NAME/KEY: misc_feature
<222> LOCATION: (20)..(20)
<223> OTHER INFORMATION: n = deoxythymidine
<220> FEATURE:
<221> NAME/KEY: misc_feature
<222> LOCATION: (21)..(21)
<223> OTHER INFORMATION: n = deoxycytidine

<400> SEQUENCE: 15
agcucauaga acaccuccgn n                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-2 alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 16
aagggcuagc aacaaaaccn n                                              21

<210> SEQ ID NO 17
<211> LENGTH: 19
<212> TYPE: RNA
<213> ORGANISM: Artificial Sequence
<220> FEATURE:
<223> OTHER INFORMATION: Synthetic sense strand of siRNA for human HIF-1
      alpha

<400> SEQUENCE: 17
ggaaccugau gcuuuaacu                                                 19

<210> SEQ ID NO 18
<211> LENGTH: 19
<212> TYPE: RNA
<213> ORGANISM: Artificial Sequence
<220> FEATURE:
<223> OTHER INFORMATION: Synthetic sense strand of siRNA for human HIF-1
      alpha

<400> SEQUENCE: 18
ggguaaagaa caaaacaca                                                 19

<210> SEQ ID NO 19
<211> LENGTH: 19
<212> TYPE: RNA
<213> ORGANISM: Artificial Sequence
<220> FEATURE:
<223> OTHER INFORMATION: Synthetic sense strand of siRNA for human HIF-1
      alpha
```

```
<400> SEQUENCE: 19
ggcagcagaa accacugc                                                     19

<210> SEQ ID NO 20
<211> LENGTH: 19
<212> TYPE: RNA
<213> ORGANISM: Artificial Sequence
<220> FEATURE:
<223> OTHER INFORMATION: Synthetic sense strand of siRNA for human HIF-1
      alpha

<400> SEQUENCE: 20
gcacgacuug auuuucucc                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic sense strand of siRNA for human HIF-2
      alpha

<400> SEQUENCE: 21
cggagguguu cuaugagcu                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic sense strand of siRNA for human HIF-2
      alpha

<400> SEQUENCE: 22
gguuuuguug cuagcccuu                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-1 alpha

<400> SEQUENCE: 23
aguuaaagca ucagguucc                                                    19

<210> SEQ ID NO 24
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-1 alpha

<400> SEQUENCE: 24
uguguuuugu ucuuuaccc                                                    19

<210> SEQ ID NO 25
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-1 alpha

<400> SEQUENCE: 25
```

-continued gcaguagguu ucugcugcc        19

<210> SEQ ID NO 26
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-1 alpha

<400> SEQUENCE: 26
ggagaaaauc aagucgugc        19

<210> SEQ ID NO 27
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-2 alpha

<400> SEQUENCE: 27
agcucauaga acaccuccg        19

<210> SEQ ID NO 28
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-2 alpha

<400> SEQUENCE: 28
aagggcuagc aacaaaacc        19

<210> SEQ ID NO 29
<211> LENGTH: 21
<212> TYPE: DNA
<213> ORGANISM: Artificial Sequence
<220> FEATURE:
<223> OTHER INFORMATION: Synthetic sense strand of siRNA for human HIF-1
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 29
ccucagugug gguauaagan n      21

<210> SEQ ID NO 30
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-1 alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 30
ucuuauaccc acacugaggn n      21

```
<210> SEQ ID NO 31
<211> LENGTH: 19
<212> TYPE: RNA
<213> ORGANISM: Artificial Sequence
<220> FEATURE:
<223> OTHER INFORMATION: Synthetic sense strand of siRNA for human HIF-1
      alpha

<400> SEQUENCE: 31
ccucagugug gguauaaga                                                    19

<210> SEQ ID NO 32
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-1 alpha

<400> SEQUENCE: 32
ucuuauaccc acacugagg                                                    19

<210> SEQ ID NO 33
<211> LENGTH: 21
<212> TYPE: DNA
<213> ORGANISM: Artificial Sequence
<220> FEATURE:
<223> OTHER INFORMATION: Synthetic sense strand of siRNA for human HIF-2
      alpha
<220> FEATURE:
<223> OTHER INFORMATION: Combined DNA/RNA
<220> FEATURE:
<221> NAME/KEY: misc_feature
<222> LOCATION: (20)..(21)
<223> OTHER INFORMATION: n = deoxythymidine

<400> SEQUENCE: 33
ggacauagua ucuuugacun n                                                 21

<210> SEQ ID NO 34
<211> LENGTH: 21
<212> TYPE: DNA
<213> ORGANISM: Artificial Sequence
<220> FEATURE:
<223> OTHER INFORMATION: Synthetic antisense strand of siRNA for human
      HIF-2 alpha
<220> FEATURE:
<223> OTHER INFORMATION: Combined DNA/RNA
<220> FEATURE:
<221> NAME/KEY: misc_feature
<222> LOCATION: (20)..(20)
<223> OTHER INFORMATION: n = deoxythymidine
<220> FEATURE:
<221> NAME/KEY: misc_feature
<222> LOCATION: (21)..(21)
<223> OTHER INFORMATION: n = deoxyguanosine

<400> SEQUENCE: 34
agucaaagau acuauguccn n                                                 21

<210> SEQ ID NO 35
<211> LENGTH: 19
<212> TYPE: RNA
<213> ORGANISM: Artificial Sequence
<220> FEATURE:
<223> OTHER INFORMATION: Synthetic sense strand of siRNA  for human
      HIF-2 alpha

<400> SEQUENCE: 35
ggacauagua ucuuugacu                                                    19
```

```
<210> SEQ ID NO 36
<211> LENGTH: 19
<212> TYPE: RNA
<213> ORGANISM: Artificial Sequence
<220> FEATURE:
<223> OTHER INFORMATION: Synthetic antisense strand of siRNA for human
      HIF-2 alpha

<400> SEQUENCE: 36
agucaaagau acuaugucc                                                    19
```

US 8,268,794 B2

PHARMACEUTICAL CONTAINING HIF-1 ALPHA AND HIF-2 ALPHA EXPRESSION INHIBITOR

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 53,634 bytes ASCII (Text) file named "706101ReplacementSequenceListing.txt," created Feb. 22, 2011.

TECHNICAL FIELD

The present invention relates to a medicament containing an HIF-1α and HIF-2α expression inhibitory substance. More particularly, the present invention relates to a therapeutic agent for retinal diseases, which contains a nucleic acid capable of inducing RNA interference and the like.

BACKGROUND ART

Hypoxia inducible factors 1 and 2 (HIF-1 and HIF-2) are heterodimers consisting of α and β subunits, and are transcription factors having a basic helix loop helix (bHLH) domain and a PAS domain in common. The expression and transcription activity of HIF markedly increase as the intracellular oxygen concentration decreases. As a target gene transactivated by HIF, VEGF (vascular endothelial cell growth factor), erythropoietin, glucose transporter, and a gene encoding enzyme of glycolysis and the like have been identified (see non-patent document 1).

Diabetic retinopathy and age-related macular degeneration are causative diseases resulting in acquired blindness, and the development of a medicament that suppresses angiogenesis found in the both diseases is currently desired. Particularly, an intraocular increase of VEGF is known to be one of the causes of angiogenesis induction, and some VEGF antagonists are under development. HIF is a transcription factor that controls expression of VEGF, and an HIF inhibitor is also expected as an angiogenesis suppressing agent.

Studies using siRNA as an HIF inhibitor have reported that expression of VEGF is suppressed by HIF-1α siRNA in HeLa cells, Hep3B cells and Kelly cells (see non-patent document 2). In addition, it has also been reported that only HIF-1α siRNA suppresses induction of VEGF expression due to hypoxia in breast cancer cells (MDA468), and suppression does not occur by HIF-2α siRNA (see non-patent document 3). Even when siRNAs for the both isoforms of HIF-1α and 2α were used in this experiment system, the induction of VEGF expression was suppressed only to the same level as the sole use of HIF-1α siRNA. In contrast, reports have documented that only HIF-2α siRNA suppresses induction of VEGF expression due to hypoxia in kidney cancer cells (786-O), and each siRNA for HIF-1α and 2α suppresses VEGF expression in kidney cancer cells (Caki-1) having tumor suppressor gene VHL (von Hippel-Lindau) (see non-patent document 4). As mentioned above, which isoform of HIF is deeply involved in VEGF production is considered to vary depending on the cell.

Heretofore, use of siRNA and antisense for HIF-1α as a therapeutic drug for age-related macular degeneration and diabetic retinopathy has been reported (see patent documents 1-3). However, use of siRNA and antisense for HIF-2α has not been reported as far as the present inventors know. In addition, it has not been reported that inhibition of both isoforms of HIF-1α and HIF-2α markedly enhances VEGF production suppressive action as compared to inhibition of one of the isoforms, nor is there reported use of a composition containing siRNA(s) or antisense(s) for both isoforms of HIF-1α and HIF-2α for retinal diseases.

patent document 1: WO2007/002718
patent document 2: WO2004/042024
patent document 3: WO2006/050734
non-patent document 1: Semenza GL (1999), Ann. Rev. Cell. Dev. Biol. 15: 551-578
non-patent document 2: Christina W et al (2004) FASEB J 12: 1462-1464
non-patent document 3: Heidi M S et al (2004) Cancer Res 63: 6130-6134
non-patent document 4: Raju RR et al (2005) Molecular and Cellular Biology 25: 5675-5686

DISCLOSURE OF THE INVENTION

Problems to be Solved by the Invention

An object of the present invention is to provide a pharmaceutical product exhibiting a high therapeutic effect in the treatment of retinal diseases associated with angiogenesis such as age-related macular degeneration, diabetic retinopathy and the like.

Means of Solving the Problems

In view of the aforementioned problems, the present inventors have conducted intensive studies and found that inhibition of both isoforms by reacting retinal pigment epithelial cells with HIF-1α siRNA and HIF-2α siRNA markedly suppresses VEGF production than by the action of siRNA for only one of the isoforms, which resulted in the completion of the present invention. Accordingly, the present invention is as follows.

[1] A therapeutic agent for a retinal disease, comprising a substance specifically inhibiting HIF-1α expression and a substance specifically inhibiting HIF-2α expression.

[2] The therapeutic agent of the aforementioned [1], wherein the aforementioned inhibitory substance is RNAi-inducing nucleic acid, antisense nucleic acid or ribozyme, or an expression vector thereof.

[3] The therapeutic agent of the aforementioned [2], wherein the aforementioned RNAi-inducing nucleic acid is siRNA.

[4] The therapeutic agent of the aforementioned [3], wherein the aforementioned siRNA for HIF-1α consists of a sense strand comprising a sequence of 17-25 continuous bases of mRNA corresponding to the base sequence of SEQ ID NO: 1 and an antisense strand comprising a sequence complementary thereto, and the aforementioned siRNA for HIF-2α consists of a sense strand comprising a sequence of 17-25 continuous bases of mRNA corresponding to the base sequence of SEQ ID NO: 3 and an antisense strand comprising a sequence complementary thereto.

[5] The therapeutic agent of the aforementioned [4], wherein the aforementioned siRNA for HIF-1α is the following (a) or (b), and siRNA for HIF-2α is the following (c) or (d):

(a) a double strand RNA composed of a sense strand comprising a base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;

(b) a double strand RNA composed of a sense strand comprising a base sequence wherein one to several bases have been added to and/or deleted from the 5' terminal and/or 3' terminal of the base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;
(c) a double strand RNA composed of a sense strand comprising the base sequence described in any of SEQ ID NO: 21, 22 and 35, and an antisense strand comprising a sequence complementary thereto, which optionally has an overhang at the terminal of the sense strand and/or the antisense strand, and has HIF-2α expression-inhibitory activity;
(d) a double strand RNA composed of a sense strand comprising a base sequence wherein one to several bases have been added to and/or deleted from the 5' terminal and/or 3' terminal of the base sequence described in any of SEQ ID NOs: 21, 22 and 35, and an antisense strand comprising a sequence complementary thereto, which optionally has an overhang at the terminal of the sense strand and/or the antisense strand, and has HIF-2α expression-inhibitory activity.
[6] The therapeutic agent of the aforementioned [4] or [5], wherein the aforementioned siRNA for HIF-1α is any of the following (1-1)-(1-5), and siRNA for HIF-2α is any of the following (2-1)-(2-3):
(1-1) a double strand RNA composed of a sense strand consisting of the base sequence described in SEQ ID NO: 5, and an antisense strand consisting of the base sequence described in SEQ ID NO: 11;
(1-2) a double strand RNA composed of a sense strand consisting of the base sequence described in SEQ ID NO: 6, and an antisense strand consisting of the base sequence described in SEQ ID NO: 12;
(1-3) a double strand RNA composed of a sense strand consisting of the base sequence described in SEQ ID NO: 7, and an antisense strand consisting of the base sequence described in SEQ ID NO: 13;
(1-4) a double strand RNA composed of a sense strand consisting of the base sequence described in SEQ ID NO: 8, and an antisense strand consisting of the base sequence described in SEQ ID NO: 14;
(1-5) a double strand RNA composed of a sense strand consisting of the base sequence described in SEQ ID NO: 29, and an antisense strand consisting of the base sequence described in SEQ ID NO: 30;
(2-1) a double strand RNA composed of a sense strand consisting of the base sequence described in SEQ ID NO: 9, and an antisense strand consisting of the base sequence described in SEQ ID NO: 15;
(2-2) a double strand RNA composed of a sense strand consisting of the base sequence described in SEQ ID NO: 10, and an antisense strand consisting of the base sequence described in SEQ ID NO: 16;
(2-3) a double strand RNA composed of a sense strand consisting of the base sequence described in SEQ ID NO: 33, and an antisense strand consisting of the base sequence described in SEQ ID NO: 34.
[7] The therapeutic agent of any of the aforementioned [1] [6], wherein the retinal disease is age-related macular degeneration, diabetic retinopathy, retinopathy of prematurity, retinal vein occlusion, retinal artery obstruction, diabetic macular edema or glaucoma.
[8] The therapeutic agent of the aforementioned [7], wherein the retinal disease is age-related macular degeneration or diabetic retinopathy.

[9] Use of a substance specifically inhibiting expression of HIF-1α and a substance specifically inhibiting expression of HIF-2α, for the production of a therapeutic agent for a retinal disease.
[10] The use of the aforementioned [9], wherein the aforementioned inhibitory substance is RNAi-inducing nucleic acid, antisense nucleic acid or ribozyme, or an expression vector thereof.
[11] The use of the aforementioned [10], wherein the aforementioned RNAi-inducing nucleic acid is siRNA.
[12] The use of the aforementioned [11], wherein the aforementioned siRNA for HIF-1α consists of a sense strand comprising a sequence of 17-25 continuous bases of mRNA corresponding to the base sequence of SEQ ID NO: 1 and an antisense strand comprising a sequence complementary thereto, and the aforementioned siRNA for HIF-2α consists of a sense strand comprising a sequence of 17-25 continuous bases of mRNA corresponding to the base sequence of SEQ ID NO: 3 and an antisense strand comprising a sequence complementary thereto.
[13] The use of the aforementioned [12], wherein the aforementioned siRNA for HIF-1α is the following (a) or (b), and siRNA for HIF-2α is the following (c) or (d):
(a) a double strand RNA composed of a sense strand comprising a base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;
(b) a double strand RNA composed of a sense strand comprising a base sequence wherein one to several bases have been added to and/or deleted from the 5' terminal and/or 3' terminal of the base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;
(c) a double strand RNA composed of a sense strand consisting of the base sequence described in any of SEQ ID NO: 21, 22 and 35, and an antisense strand comprising a sequence complementary thereto, which optionally has an overhang at the terminal of the sense strand and/or the antisense strand, and has HIF-2α expression-inhibitory activity;
(d) a double strand RNA composed of a sense strand comprising a base sequence wherein one to several bases have been added to and/or deleted from the 5' terminal and/or 3' terminal of the base sequence described in any of SEQ ID NOs: 21, 22 and 35, and an antisense strand comprising a sequence complementary thereto, which optionally has an overhang at the terminal of the sense strand and/or the antisense strand, and has HIF-2α expression-inhibitory activity.
[14] The use of the aforementioned [12] or [13], wherein the aforementioned siRNA for HIF-1α is any of the following (1-1)-(1-5), and siRNA for HIF-2α is any of the following (2-1)-(2-3):
(1-1) a double strand RNA composed of a sense strand consisting of the base sequence described in SEQ ID NO: 5, and an antisense strand consisting of the base sequence described in SEQ ID NO: 11;
(1-2) a double strand RNA composed of a sense strand consisting of the base sequence described in SEQ ID NO: 6, and an antisense strand consisting of the base sequence described in SEQ ID NO: 12;
(1-3) a double strand RNA composed of a sense strand consisting of the base sequence described in SEQ ID NO: 7, and an antisense strand consisting of the base sequence described in SEQ ID NO: 13;

(1-4) a double strand RNA composed of a sense strand consisting of the base sequence described in SEQ ID NO: 8, and an antisense strand consisting of the base sequence described in SEQ ID NO: 14;
(1-5) a double strand RNA composed of a sense strand consisting of the base sequence described in SEQ ID NO: 29, and an antisense strand consisting of the base sequence described in SEQ ID NO: 30;
(2-1) a double strand RNA composed of a sense strand consisting of the base sequence described in SEQ ID NO: 9, and an antisense strand consisting of the base sequence described in SEQ ID NO: 15;
(2-2) a double strand RNA composed of a sense strand consisting of the base sequence described in SEQ ID NO: 10, and an antisense strand consisting of the base sequence described in SEQ ID NO: 16;
(2-3) a double strand RNA composed of a sense strand consisting of the base sequence described in SEQ ID NO: 33, and an antisense strand consisting of the base sequence described in SEQ ID NO: 34.

[15] The use of any of the aforementioned [9]-[14], wherein the retinal disease is age-related macular degeneration, diabetic retinopathy, retinopathy of prematurity, retinal vein occlusion, retinal artery obstruction, diabetic macular edema or glaucoma.

[16] The use of the aforementioned [15], wherein the retinal disease is age-related macular degeneration or diabetic retinopathy.

[17] A method of treating a retinal disease, comprising a step of administering an effective amount of a substance specifically inhibiting expression of HIF-1α and an effective amount of a substance specifically inhibiting expression of HIF-2α to a subject in need of a treatment of retinal disease.

[18] The method of the aforementioned [17], wherein the aforementioned inhibitory substance is RNAi-inducing nucleic acid, antisense nucleic acid or ribozyme, or an expression vector thereof.

[19] The method of the aforementioned [18], wherein the aforementioned RNAi-inducing nucleic acid is siRNA.

[20] The method of the aforementioned [19], wherein the aforementioned siRNA for HIF-1α consists of a sense strand comprising a sequence of 17-25 continuous bases of mRNA corresponding to the base sequence of SEQ ID NO: 1 and an antisense strand comprising a sequence complementary thereto, and the aforementioned siRNA for HIF-2α consists of a sense strand comprising a sequence of 17-25 continuous bases of mRNA corresponding to the base sequence of SEQ ID NO: 3 and an antisense strand comprising a sequence complementary thereto.

[21] The method of the aforementioned [19], wherein the aforementioned siRNA for HIF-1α is the following (a) or (b), and siRNA for HIF-2α is the following (c) or (d):
(a) a double strand RNA composed of a sense strand comprising a base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;
(b) a double strand RNA composed of a sense strand comprising a base sequence wherein one to several bases have been added to and/or deleted from the 5' terminal and/or 3' terminal of the base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;
(c) a double strand RNA composed of a sense strand comprising the base sequence described in any of SEQ ID NO: 21, 22 and 35, and an antisense strand comprising a sequence complementary thereto, which optionally has an overhang at the terminal of the sense strand and/or the antisense strand, and has HIF-2α expression-inhibitory activity;
(d) a double strand RNA composed of a sense strand comprising a base sequence wherein one to several bases have been added to and/or deleted from the 5' terminal and/or 3' terminal of the base sequence described in any of SEQ ID NOs: 21, 22 and 35, and an antisense strand comprising a sequence complementary thereto, which optionally has an overhang at the terminal of the sense strand and/or the antisense strand, and has HIF-2α expression-inhibitory activity.

[22] The method of the aforementioned [19], wherein the aforementioned siRNA for HIF-1α is any of the following (1-1)-(1-5), and siRNA for HIF-2α is any of the following (2-1)-(2-3):
(1-1) a double strand RNA composed of a sense strand consisting of the base sequence described in SEQ ID NO: 5, and an antisense strand consisting of the base sequence described in SEQ ID NO: 11;
(1-2) a double strand RNA composed of a sense strand consisting of the base sequence described in SEQ ID NO: 6, and an antisense strand consisting of the base sequence described in SEQ ID NO: 12;
(1-3) a double strand RNA composed of a sense strand consisting of the base sequence described in SEQ ID NO: 7, and an antisense strand consisting of the base sequence described in SEQ ID NO: 13;
(1-4) a double strand RNA composed of a sense strand consisting of the base sequence described in SEQ ID NO: 8, and an antisense strand consisting of the base sequence described in SEQ ID NO: 14;
(1-5) a double strand RNA composed of a sense strand consisting of the base sequence described in SEQ ID NO: 29, and an antisense strand consisting of the base sequence described in SEQ ID NO: 30;
(2-1) a double strand RNA composed of a sense strand consisting of the base sequence described in SEQ ID NO: 9, and an antisense strand consisting of the base sequence described in SEQ ID NO: 15;
(2-2) a double strand RNA composed of a sense strand consisting of the base sequence described in SEQ ID NO: 10, and an antisense strand consisting of the base sequence described in SEQ ID NO: 16;
(2-3) a double strand RNA composed of a sense strand consisting of the base sequence described in SEQ ID NO: 33, and an antisense strand consisting of the base sequence described in SEQ ID NO: 34.

[23] The method of the aforementioned [17], wherein the retinal disease is age-related macular degeneration, diabetic retinopathy, retinopathy of prematurity, retinal vein occlusion, retinal artery obstruction, diabetic macular edema or glaucoma.

[24] The method of the aforementioned [23], wherein the retinal disease is age-related macular degeneration or diabetic retinopathy.

Effect of the Invention

Using the therapeutic agent for retinal disease of the present invention, which specifically inhibits expression of both HIF-1α and HIF-2α, production of VEGF in retinal cells can be effectively suppressed as compared to inhibition of either of them. The suppressive effect on VEGF production is synergistic. The therapeutic agent for retinal disease of the present invention can be expected to afford a superior effect as compared to conventional nucleic acid medicaments.

BEST MODE FOR CARRYING OUT THE INVENTION

Figure 1:
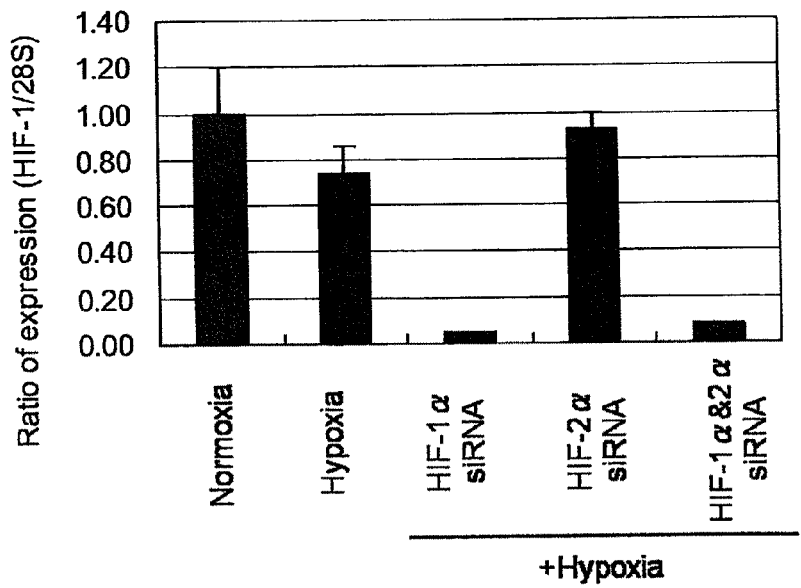
FIG. 1 is a graph showing the expression level of HIF-1α in RPE cells.

VEGF is a factor that specifically acts on receptors (Flt-1, KDR/Flk-1 etc.) present on the vascular endothelial cell surface to promote construction of a blood capillary network by growth, migration and lumen formation of vascular endothelial cells, and plays an extremely important role in the development of angiogenesis (Ferrara, N. et al. Kidney Int. 1999, 56, 794-814). In addition, it is known that VEGF is an important control factor of angiogenesis and blood vessel permeability in ocular tissues, and involved in retinal diseases such as age-related macular degeneration, diabetic retinopathy and the like (Shams, N. et al. Ophthalmol. Clin. North. Am. 2006, 19, 335-344). The therapeutic agent of the present invention can specifically inhibit expression of HIF-1α la and HIF-2α that control VEGF expression at the upstream, in the cells derived from the retina such as retinal pigment epithelial cell, Muller cell and the like. Since the therapeutic agent of the present invention suppresses VEGF production and controls development of angiogenesis, it is useful as a therapeutic agent for retinal diseases, particularly as a therapeutic agent for retinal diseases associated with angiogenesis. Specific examples of the retinal diseases associated with angiogenesis include age-related macular degeneration, diabetic retinopathy, retinopathy of prematurity, retinal vein occlusion, retinal artery obstruction, diabetic macular edema, glaucoma (particularly angiogenesis glaucoma) and the like. Since increase of VEGF in retinal pigment epithelial cells is known to be one of the causes of angiogenesis observed in age-related macular degeneration (Katrina et al. Am. J. Pathol. 2000, 157, 135-144), the therapeutic agent of the present invention exhibiting a superior suppressive action on VEGF production in retinal pigment epithelial cells is particularly useful as a therapeutic agent for age-related macular degeneration.

In the present invention, HIF-1α and HIF-2α are transcription factors derived from any mammal. Examples of the mammal include human and mammals other than human. Examples of the mammal other than human include experimental animals such as rodents (e.g., mouse, rat, hamster, guinea pig and the like), rabbit and the like, domestic animals such as swine, bovine, goat, horse, sheep and the like, pet animals such as dog, cat and the like, and primates such as monkey, orangutan, chimpanzee and the like. For the treatment of human diseases, HIF-1α and HIF-2α derived from human are preferable. HIF-2α is also referred to as EPAS1 or HLF. The base sequence and amino acid sequence of human HIF-1α and HIF-2α are known and, for example, the base sequence (SEQ ID NO: 1) and amino acid sequence (SEQ ID NO: 2) of HIF-1α (GenBank Accession No. NM_001530), and the base sequence (SEQ ID NO: 3) and amino acid sequence (SEQ ID NO: 4) of HIF-2α (GenBank Accession No. NM_001430) and the like are registered in and published by GenBank.

The therapeutic agent of the present invention characteristically contains a substance specifically inhibiting expression of HIF-1α and a substance specifically inhibiting expression of HIF-2α.

The substance specifically inhibiting expression of HIF-1α, which is contained in the therapeutic agent of the present invention as an active ingredient, is not particularly limited as long as it acts in the HIF-1α transcription process and specifically inhibits the expression thereof. In addition, the substance specifically inhibiting expression of HIF-2α, which is contained in the therapeutic agent of the present invention as an active ingredient, is not particularly limited as long is as it acts in HIF-2α transcription process and specifically inhibits the expression thereof. Examples of such inhibitory substance include RNAi-inducing nucleic acid, antisense nucleic acid and ribozyme, and an expression vector thereof.

The aforementioned RNAi-inducing nucleic acid refers to a polynucleotide capable of inducing RNA interference by being introduced into the cell, and is preferably RNA or a chimera molecule of RNA and DNA. The RNA interference refers to an effect of RNA having a double strand structure containing the same base sequence as that of mRNA (or a partial sequence thereof) to suppress expression of the mRNA. To achieve the RNAi effect, for example, RNA having a double strand structure containing the same base sequence as that of the target mRNA of at least 19 contiguous bases (or a partial sequence thereof) is preferably used. As long as it shows an HIF-1α or HIF-2α expression-inhibitory activity, several bases thereof may be substituted or RNA shorter than 19 bases in length may be used. The double strand structure may consists of different strands of a sense strand and an antisense strand, or may be a double strand (shRNA) formed by a stem loop structure of one RNA. Examples of the RNAi-inducing nucleic acid include siRNA, miRNA and the like.

In view of a strong transcription suppressive activity, preferable RNAi-inducing nucleic acid is siRNA. siRNA for HIF-1α or HIF-2α can target any part of mRNA of HIF-1α or HIF-2α. siRNA molecule for HIF-1α or HIF-2α is not particularly limited as long as it can induce an RNAi effect and, for example, 17-25 bases in length, preferably 17-23 bases in length, more preferably 17-21 bases in length. siRNA for HIF-1α or HIF-2α is a double strand containing a sense strand and an antisense strand. Specifically, siRNA for HIF-1α consists of a sense strand comprising a sequence of 17-25 (preferably 17-23, more preferably 17-21) contiguous bases of mRNA corresponding to the base sequence of SEQ ID NO: 1 and an antisense strand comprising a sequence complementary thereto. Preferably, it consists of a sense strand comprising a sequence of 17-25 (preferably 17-23, more preferably 17-21) contiguous bases targeting the 906th to 1478th of SEQ ID NO: 1 and an antisense strand comprising a sequence complementary thereto. siRNA for HIF-2α consists of a sense strand comprising a sequence of 17-25 (preferably 17-23, more preferably 17-21) contiguous bases of mRNA corresponding to the base sequence of SEQ ID NO: 3 and an antisense strand comprising a sequence complementary thereto. Preferably, it consists of a sense strand comprising a sequence of 17-25 (preferably 17-23, more preferably 17-21) contiguous bases targeting the 580th to 4242nd of SEQ ID NO: 3 and an antisense strand comprising a sequence complementary thereto. siRNA for HIF-1α or HIF-2α optionally has an overhang at the 5' terminal or 3' terminal of one or both of the sense strand and antisense strand. The overhang is formed by the addition of one to several (e.g., 1, 2 or 3) bases to the terminal of the sense strand and/or antisense strand. The design method of siRNA is known to those of ordinary skill in the art, and an appropriate base sequence of siRNA can be selected from the above-mentioned base sequences by using various design software or algorithms of siRNA. Since mRNAs of HIF-1α and HIF-2α are highly homologous, siRNA capable of simultaneous knock down of the both mRNAs can also be selected. In this case, the nucleic acid contained in the therapeutic agent of the present invention may be of one kind.

(1) HIF-1α siRNA

A specific siRNA sequence for HIF-1α is preferably a double strand RNA defined by the following (a) or (b) based on the base sequence of the following SEQ ID NO: 17-20 or 31.

(a) a double strand RNA composed of a sense strand comprising a base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;

(b) a double strand RNA composed of a sense strand comprising a base sequence wherein one to several bases have been added to and/or deleted from the 5' terminal and/or 3' terminal of the base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity. Here, the addition and/or deletion of one to several (e.g., 1-5, preferably 1-3, more preferably 1 or 2) bases at the 5' terminal and/or 3' terminal of the base sequence described in any of SEQ ID NOs: 17-20 and 31 can be achieved such that the identity with a partial base sequence of a sense strand encoding HIF-1α gene and an antisense strand thereof is secured so as to retain the HIF-1α expression-inhibitory activity.

Of the siRNAs to HIF-1α, siRNA having an overhang is preferably one of the following (1-1)-(1-5) (underline shows overhang):

(1-1) a double strand RNA composed of a sense strand consisting of the base sequence described in SEQ ID NO: 5 (5'-ggaac cugau gcuuu aacutt-3'), and an antisense strand consisting of the base sequence described in SEQ ID NO: 11 (5'-aguua aagca ucagg uucctt-3');

(1-2) a double strand RNA composed of a sense strand consisting of the base sequence described in SEQ ID NO: 6 (5'-gggua aagaa caaaa cacatt-3'), and an antisense strand consisting of the base sequence described in SEQ ID NO: 12 (5'-ugugu uuugu ucuuu accctt-3');

(1-3) a double strand RNA composed of a sense strand consisting of the base sequence described in SEQ ID NO: 7 (5'-ggcagcagaaaccuacugctt-3'), and an antisense strand consisting of the base sequence described in SEQ ID NO: 13 (5'-gcaguagguuucugcugcctt-3');

(1-4) a double strand RNA composed of a sense strand consisting of the base sequence described in SEQ ID NO: 8 (5'-gcacgacuugauuuucucctt-3'), and an antisense strand consisting of the base sequence described in SEQ ID NO: 14 (5'-ggagaaaaucaagucgugctg-3');

(1-5) a double strand RNA composed of a sense strand consisting of the base sequence described in SEQ ID NO: 29 (5'-ccucagugugggguauaagatt-3'), and an antisense strand consisting of the base sequence described in SEQ ID NO: 30 (5'-ucuuauacccacacugaggtt-3').

(2) HIF-2α siRNA

A specific siRNA sequence for HIF-2α is preferably a double strand RNA defined by the following (c) or (d) based on the base sequence of the following SEQ ID NO: 21, 22 or 35.

(c) a double strand RNA composed of a sense strand consisting of the base sequence described in any of SEQ ID NO: 21, 22 and 35, and an antisense strand comprising a sequence complementary thereto, which optionally has an overhang at the terminal of the sense strand and/or the antisense strand, and has HIF-2α expression-inhibitory activity;

(d) a double strand RNA composed of a sense strand comprising a base sequence wherein one to several bases have been added to and/or deleted from the 5' terminal and/or 3' terminal of the base sequence described in any of SEQ ID NOs: 21, 22 and 35, and an antisense strand comprising a sequence complementary thereto, which optionally has an overhang at the terminal of the sense strand and/or the antisense strand, and has HIF-2α expression-inhibitory activity. Here, the addition and/or deletion of one to several (e.g., 1-5, preferably 1-3, more preferably 1 or 2) bases at the 5' terminal and/or 3' terminal of the base sequence described in any of SEQ ID NOs: 21, 22 and 35 can be achieved such that the identity with a partial base sequence of a sense strand encoding HIF-2α gene and an antisense strand thereof is secured so as to retain the HIF-2α expression-inhibitory activity.

TABLE 1

| siRNA sense strand (SEQ ID NO) | antisense strand* (SEQ ID NO) |
|---|---|
| HIF-1α 5'-ggaac cugau gcuuu aacu-3' (17) | 5'-aguua aagca ucagg uucc-3' (23) |
| HIF-1α 5'-gggua aagaa caaaa caca-3' (18) | 5'-ugugu uuugu ucuuu accc-3' (24) |
| HIF-1α 5'-ggcag cagaa accua cugc-3' (19) | 5'-gcagu agguu ucugc ugcc-3' (25) |
| HIF-1α 5'-gcacg acuug auuuu cucc-3' (20) | 5'-ggaga aaauc aaguc gugc-3' (26) |
| HIF-1α 5'-ccuca gugug gguau aaga-3' (31) | 5'-ucuua uaccc acacu gagg-3' (32) |

*antisense strand sequence is one embodiment to sense strand sequence in the left column

TABLE 2

| siRNA sense strand (SEQ ID NO) | antisense strand* (SEQ ID NO) |
|---|---|
| HIF-2α 5'-cggag guguu cuaug agcu-3' (21) | 5'-agcuc auaga acacc uccg-3' (27) |
| HIF-2α 5'-gguuu uguug cuagc ccuu-3' (22) | 5'-aaggg cuagc aacaa aacc-3' (28) |
| HIF-2α 5'-ggaca uagua ucuuu gacu-3' (35) | 5'-aguca aagau acuau gucc-3' (36) |

*antisense strand sequence is one embodiment to sense strand sequence in the left column Of the siRNAs to HIF-2α, siRNA having an overhang is preferably one of the following (2-1)-(2-3) (underline shows overhang):
(2-1) a double strand RNA composed of a sense strand consisting of the base sequence described in SEQ ID NO: 9 (5'-cggag guguu cuaug agcutt-3'), and an antisense strand consisting of the base sequence described in SEQ ID NO: 15 (5'-agcuc auaga acacc uccgtc-3');
(2-2) a double strand RNA composed of a sense strand consisting of the base sequence described in SEQ ID NO: 10 (5'-gguuu uguug cuagc ccuutt-3'), and an antisense strand consisting of the base sequence described in SEQ ID NO: 16 (5'-aaggg cuagc aacaa aacctt-3');
(2-3) a double strand RNA composed of a sense strand consisting of the base sequence described in SEQ ID NO: 33 (5'-ggaca uagua ucuuu gacutt-3'), and an antisense strand consisting of the base sequence described in SEQ ID NO: 34 (5'-aguca aagau acuau gucctg-3').

The antisense nucleic acid to HIF-1α or antisense nucleic acid to HIF-2α refers to a polynucleotide consisting of a base sequence capable of hybridizing with a transcription product under physiological conditions of cells that express transcription products (mRNA or initial transcription product) of HIF-1α or HIF-2α, which can inhibit translation of polypeptide encoded by the transcription product in a hybridized state. The kind of the antisense nucleic acid may be DNA or RNA, or DNA/RNA chimera. The antisense nucleic acid may have a natural-type phosphodiester bond or may be a modified nucleotide such as thiophosphoric acid type (P=O of phosphate bond is substituted by P=S), 2'-O-methyl type, which are stable to degrading enzymes and the like. Other elements important for the design of the antisense nucleic acid include enhancement of water-solubility and cell membrane permeability and the like, and these can also be overcome by a dosage form design such as use of liposome and microsphere, and the like. The length of the antisense nucleic acid is not particularly limited as long as specific hybridization with the transcription products of HIF-1α or HIF-2α (e.g., mRNA corresponding to the base sequence of SEQ ID NO: 1 or SEQ ID NO: 3) is possible. A short sequence may contain about 15 bases, and a long sequence may contain a sequence complementary to the whole sequence of the transcription product. In consideration of easy synthesis, antigenicity problem and the like, for example, an oligonucleotide consisting of about 15 bases or more, preferably about 15-about 30 bases, more preferably about 18 bases-about 30 bases, can be mentioned. Furthermore, the antisense nucleic acid may be one which not only inhibits translation by hybridizing with a transcription product of HIF-1α or HIF-2α, but can also inhibit transcription to mRNA by binding with double stranded DNA to form a triple strand (triplex). The antisense nucleic acid to HIF-1α preferably contains the base sequence described in any of SEQ ID NOs: 1 base sequence described in any of SEQ ID NOs: 21, 22 and 35-20, 23-26, 31 and 32 (when the antisense nucleic acid is DNA, U is T). The antisense nucleic acid to HIF-2α preferably contains the base sequence described in any of SEQ ID NOs: 21, 22, 2 base sequence described in any of SEQ ID NOs: 21, 22 and 35, 28, 35 and 36 (when the antisense nucleic acid is DNA, U is T).

In the present specification, being "complementary" means having complementarity of not less than about 70%, preferably not less than about 80%, more preferably not less than about 90%, more preferably not less than about 95%, most preferably 100%, between base sequences. The homology of the base sequence in the present specification can be calculated under the following conditions (expectation value=10; gaps are allowed; filtering=ON; match score=1; mismatch score=-3) using a homology scoring algorithm NCBI BLAST (National Center for Biotechnology Information Basic Local Alignment Search Tool).

The aforementioned "ribozyme" refers to RNA having enzymatic activity for cleaving nucleic acid, but the present specification also includes DNA as long as there is a sequence specific enzymatic activity for cleaving nucleic acid, since it has recently been clarified that oligoDNA having a base sequence of the enzyme active site similarly shows a nucleic acid cleaving activity. To be precise, ribozyme can specifically cleave mRNA encoding HIF-1α or HIF-2α or initial transcription product within the coding region (including intron site in case of initial transcription product). Ribozyme having broadest utility includes self-splicing RNA seen in infectious RNA, such as viroid, virusoid and the like, and hammerhead type, hairpin type and the like are known. The hammerhead type exhibits an enzyme activity with about 40 bases, and can specifically cleave only a target mRNA by forming, with several bases on both ends (total of about 10 bases) adjacent to the hammerhead structure, sequences complementary to desired cleavage sites of the mRNA. When ribozyme is used in the form of an expression vector containing a DNA encoding the same, to promote transfer of a transcription product to the cytoplasm, a hybrid ribozyme wherein a sequence of altered tRNA is ligated can also be formed (Nucleic Acids Res., 29(13): 2780-2788 (2001)).

HIF-1α and HIF-2α specific inhibitory substances can also be provided as expression vectors. Such expression vectors contain polynucleotides encoding HIF-1α and HIF-2α specific inhibitory substances, and promoters operably linked to the polynucleotides.

The aforementioned promoter can be appropriately selected according to the kind of the nucleic acid of the expression target under its control and, for example, polIII promoters (e.g., tRNA promoter, U6 promoter, H1 promoter), mammalian promoters (e.g., CMV promoter, CAG promoter, SV40 promoter) can be mentioned.

The expression vector of the present invention may further contain a selection marker gene (gene imparting resistance to drugs such as tetracycline, ampicillin, kanamycin, hygromycin, phosphinothricin and the like, gene complementing auxotrophic mutation etc.).

While the backbone of the expression vector of the present invention is not particularly limited as long as it can produce HIF-1α and HIF-2α specific inhibitory substances in mammalian (human and the like) cells. For example, plasmid vector and virus vector can be mentioned. As a vector preferable for administration to mammals, virus vectors such as retrovirus, adenovirus, adeno-associated virus, herpes virus, vaccinia virus, pox virus, polio virus, Sindbis virus, Hemagglutinating Virus of Japan and the like can be mentioned. Among these, virus vectors derived from retrovirus, adenovirus, adeno-associated virus or vaccinia virus are preferable.

While the dose of the therapeutic agent of the present invention varies depending on the kind or activity of the active ingredient, animal species to be the subject of administration, severity of the disease of the subject of administration, drug tolerance, body weight, age and the like, it is generally about 0.0001-about 1000 mg/kg for an adult per day in the amount of the active ingredient.

The subject of administration of the therapeutic agent of the present invention includes human and mammals other than human and, examples of the mammals other than human include experimental animals such as rodents such as mouse, rat, hamster, guinea pig and the like, rabbit and the like, domestic animals such as swine, bovine, goat, horse, sheep and the like, pet animals such as dog, cat and the like, and primates such as monkey, orangutan, chimpanzee and the like.

The therapeutic agent of the present invention can be orally or parenterally administered to patients. The administration form is, for example, oral administration, topical administration to the eye (instillation administration, intravitreal administration, subconjunctival administration, subtenon administration etc.), intravenous administration, transdermal administration and the like and, where necessary, a dosage form suitable for administration is formed along with a pharmaceutically acceptable additive. Examples of the dosage form suitable for oral administration include tablet, capsule, granule, powder and the like, and examples of the dosage form suitable for parenteral administration include eye drop, eye ointment, injection, adhesive preparation, lotion, cream and the like. They can be prepared by conventional techniques widely used in the art. The administration route and dosage form of the therapeutic agent of the present invention are not particularly limited as long as the aforementioned treatment effect can be afforded. Preferable administration route is topical administration to the eye, and the dosage form thereof is injection or eye drop.

In addition, the therapeutic agent of the present invention can also be formulated into, besides those preparations, a preparation for intraocular implantation, DDS (drug delivery system) preparation such as microsphere and the like.

For example, when the therapeutic agent of the present invention is used as an injection or eye drop, stabilizers (e.g., sodium bisulfite, sodium thiosulfate, sodium edetate, to sodium citrate, ascorbic acid, dibutylhydroxytoluene and the like), solubilizing agents (e.g., glycerol, propylene glycol, macrogol, polyoxyethylene hydrogenated castor oil and the like), suspending agents (e.g., polyvinylpyrrolidone, hydroxypropylmethylcellulose, hydroxymethylcellulose, sodium carboxymethylcellulose and the like), emulsifiers (e.g., polyvinylpyrrolidone, soybean lecithin, egg-yolk lecithin, polyoxyethylene hydrogenated castor oil, polysorbate 80 and the like), buffers (e.g., phosphate buffer, acetate buffer, borate buffer, carbonate buffer, citrate buffer, tris buffer, glutamic acid, epsilon-aminocaproic acid and the like), thickeners (e.g., water-soluble cellulose derivatives such as methylcellulose, hydroxyethylcellulose, hydroxypropylmethylcellulose, carboxymethylcellulose and the like, sodium chondroitin sulfate, sodium hyaluronate, carboxyvinyl polymer, polyvinyl alcohol, polyvinylpyrrolidone, macrogol and the like), preservatives (e.g., benzalkonium chloride, benzethonium chloride, chlorhexidine gluconate, chlorobutanol, benzyl alcohol, sodium dehydroacetate, paraoxybenzoates, sodium edetate, boric acid and the like), isotonicity agents (e.g., sodium chloride, potassium chloride, glycerol, mannitol, sorbitol, boric acid, glucose, propylene glycol and the like), pH adjusters (e.g., hydrochloric acid, sodium hydroxide, phosphoric acid, acetic acid and the like), algefacients (e.g., l-menthol, d-camphor, d-borneol, peppermint oil and the like), ointment bases (white petrolatum, purified lanolin, liquid paraffin, vegetable oil (olive oil, camellia oil, peanuts oil and the like) and the like) and the like can be used as additives. While the amount of these additives to be added varies depending on the kind, use and the like of the additives to be added, they can be added at concentrations capable of achieving the object of the additive.

The therapeutic agent of the present invention can also be formulated using a nucleic acid such as siRNA and the like by a lipofection method. For the lipofection method, a liposome made of phosphatidylserine is generally used. Since phosphatidylserine has negative charge, a cationic lipid of N-[1-(2,3-dioleyloxy)propyl]-N,N,N-trimethylammonium chloride (DOTMA) (trade name: TRANSFECTAM, Lipofectamine) that easily affords more stable liposome is preferably used as a substitute for phosphatidylserine. By forming a complex of such cationic lipid and nucleic acid having a negative charge, such as siRNA and the like, a liposome positively charged as a whole is adsorbed to the surface of negatively charged cells and fused with the cellular membrane, whereby the nucleic acid can be introduced into the cells.

EXAMPLES

The present invention is explained in more detail in the following by referring to Examples, which are not to be construed as limitative.

Formulation Example 1

Injection for Intravitreal Administration

An injection for intravitreal administration shown below is prepared according to a conventional method.

```
HIF-1α siRNA:
sense-GGA ACC UGA UGC UUU AAC UTT      (SEQ ID NO: 5)    1 mg antisense-AGU UAA AGC AUC AGG UUC CTT  (SEQ ID NO: 11)   1 mg HIF-2α siRNA:
sense-CGG AGG UGU UCU AUG AGC UTT      (SEQ ID NO: 9)    1 mg antisense-AGC UCA UAG AAC ACC UCC GTC  (SEQ ID NO: 15)   1 mg sodium dihydrogen phosphate                              0.1 g
```

-continued

| | |
|---|---|
| sodium chloride | 0.9 g |
| sodium hydroxide | e.q. |
| sterile purified water | e.q. |
| total amount | 100 mL (pH 7) |

Formulation Example 2

Injection for Intravitreal Administration

An injection for intravitreal administration shown below is prepared according to a conventional method.

| | | |
|---|---|---|
| HIF-1α siRNA: | | |
| sense-GGG UAA AGA ACA AAA CAC ATT | (SEQ ID NO: 6) | 0.1 mg |
| antisense-UGU GUU UUG UUC UUU ACC CTT | (SEQ ID NO: 12) | 0.1 mg |
| HIF-2α siRNA: | | |
| sense-GGU UUU GUU GCU AGC CCU UTT | (SEQ ID NO: 10) | 0.1 mg |
| antisense-AAG GGC UAG CAA CAA AAC CTT | (SEQ ID NO: 16) | 0.1 mg |
| sodium dihydrogen phosphate | | 0.1 g |
| glycerol | | 2.5 g |
| sodium hydroxide | | e.q. |
| sterile purified water | | e.q. |
| total amount | | 100 mL (pH 7) |

Formulation Example 3

Injection for Subtenon Administration

An injection for subtenon administration shown below is prepared according to a conventional method.

| | | |
|---|---|---|
| HIF-1α siRNA: | | |
| sense-GGC AGC AGA AAC CUA CUG CTT | (SEQ ID NO: 7) | 5 mg |
| antisense-GCA GUA GGU UUC UGC UGC CTT | (SEQ ID NO: 13) | 5 mg |
| HIF-2α siRNA: | | |
| sense-GGA CAU AGU AUC UUU GAC UTT | (SEQ ID NO: 33) | 5 mg |
| antisense-AGU CAA AGA UAC UAU GUC CTG | (SEQ ID NO: 34) | 5 mg |
| sodium dihydrogen phosphate | | 0.1 g |
| sodium chloride | | 0.9 g |
| sodium hydroxide | | e.q. |
| sterile purified water | | e.q. |
| total amount | | 100 mL (pH 7) |

Experimental Example 1

Effect of HIF siRNA for VEGF Expression Induction in Retinal Pigment Epithelial (RPE) Cells 1. Method
1) Transfection of HIF siRNA to RPE cells RPE cells (ATCC, cell name: ARPE-19, catalog No.: CRL-2302) were seeded on a 6-well plate, cultured to 30-50% cell density, and changed to low serum medium (DMEM/F12 medium containing 0.1% FBS, Invitrogen). Each of the following HIF siRNAs was a product of Ambion (underlines show overhang consisting of deoxy form).

```
HIF-1α siRNA:
                                         (SEQ ID NO: 5)
sense-GGA ACC UGA UGC UUU AAC UTT, (SEQ ID NO: 11)
antisense-AGU UAA AGC AUC AGG UUC CTT, HIF-2α siRNA:
                                         (SEQ ID NO: 9)
sense-CGG AGG UGU UCU AUG AGC UTT,
and (SEQ ID NO: 15)
antisense-AGC UCA UAG AAC ACC UCC GTC
```

Complex of a transfection reagent (RNAi MAX, Invitrogen) was formed by stirring various siRNAs and transfection reagents in Opti-MEM (Invitrogen), followed by incubation for 25 min. Thereafter, RPE cells were cultivated in a medium controlled to a final concentration of each siRNA of 5 nM for 24 hr to transfect siRNA. Grouping was performed as follows.
(a) normoxia group
(b) hypoxia group
(c) hypoxia+drug group (HIF-1α siRNA 5 nM)
(d) hypoxia+drug group (HIF-2α siRNA 5 nM)
(e) hypoxia+drug group (HIF-1α siRNA 5 nM+HIF-2α siRNA 5 nM)
2) Culture of RPE Cells in Hypoxia System HIF siRNA was transfected into RPE cells, and subjected to hypoxic culture for 1 day using AnaeroPack for Cell (MITSUBISHI GAS CHEMICAL COMPANY, INC.). The cells cultured under normal oxygen concentration were used as a normoxia group.
3) RNA Extraction and Real-Time PCR Total RNA was extracted with a TRIzol solution (Invitrogen, catalog No.: 15596-026, 1 mL) from the RPE cells seeded in the 6-well plate. The extraction method followed the protocol of the explanatory leaflet attached to the TRIzol solution. Then, using DNA-free (Ambion), genome DNA contained in the total RNA after extraction was removed, and a reverse transcription reaction was performed using SuperScript II (Invitrogen) and Random primer (Ambion). Thereafter, the obtained cDNA solution was subjected to a Real-time PCR reaction using TaqMan Universal PCR master mix (Applied Biosystems). As the primer, a TaqMan Real-time PCR primer manufactured by Applied Biosystems (HIF-1α: Hs00153153_ml, HIF-2α: Hs01026142_ml, VEGF: Hs00173626_ml) was used.
2. Results and Discussion Whether addition of each of HIF-1α siRNA, HIF-2α siRNA and mixed siRNA of the both isoforms suppresses hyperexpression of VEGF due to a hypoxic treatment was examined using the RPE cells.

Figure 2:
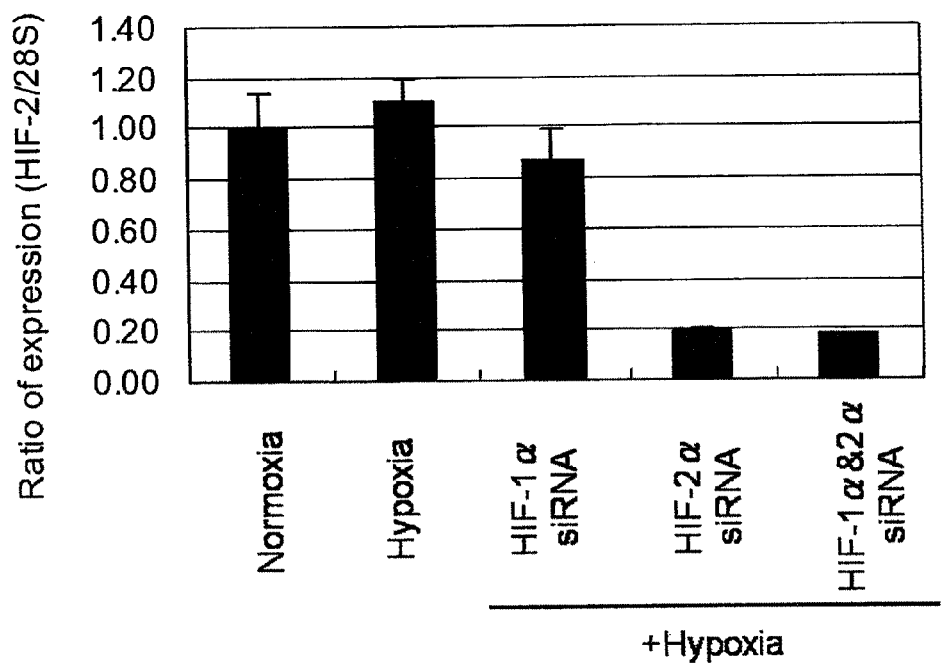
FIG. 2 is a graph showing the expression level of HIF-2α in RPE cells.
Figure 3:
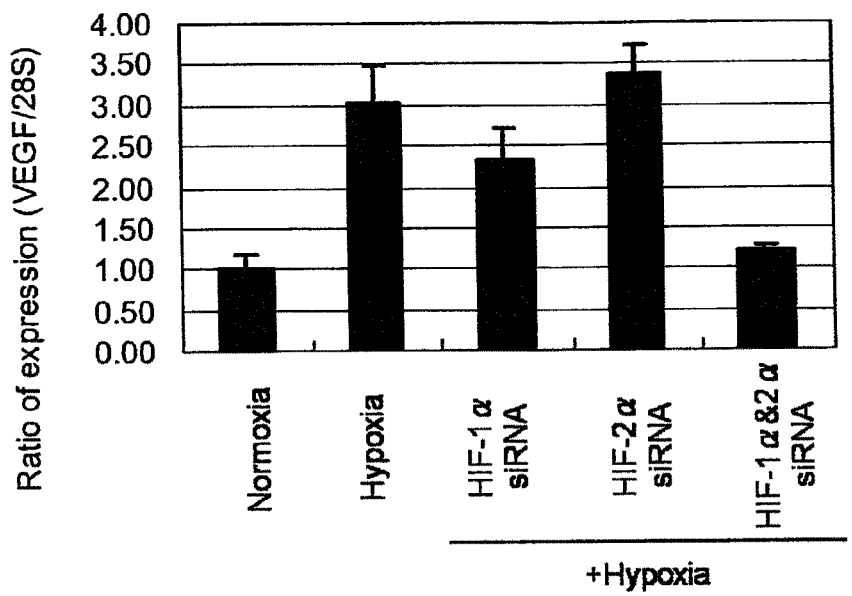
FIG. 3 is a graph showing the expression level of VEGF in RPE cells.

FIG. 1 shows the expression level of HIF-1α. By the addition of HIF-1α siRNA alone or mixed siRNA consisting of the both isoforms, inhibition of HIF-1α expression was observed. On the other hand, FIG. 2 shows the expression level of HIF-2α, where the addition of HIF-2α siRNA alone, or mixed siRNA consisting of the both isoforms revealed inhibition of HIF-2α expression. Under the same conditions, suppression of VEGF expression was confirmed as shown in FIG. 3. While the sole addition of HIF-1α siRNA showed suppression of VEGF expression, the suppressive effect thereof was insufficient and was 35%. On the other hand, with HIF-2α siRNA alone, a suppressive effect was not observed at all. However, a group supplemented with the both isoforms of HIF-1α and 2α showed a remarkable VEGF expression suppressive effect, which was not even expected by sole addition, and the suppression rate was 89%. From the above-mentioned results, when angiogenesis in the retina is to be suppressed by inhibiting HIF, it is desirable to inhibit the both isoforms, unlike in other cells.

Experimental Example 2

Effect of HIF siRNA to VEGF Expression Induction in Retinal Pigment Epithelial (RPE) Cells 1. Method
1) Transfection of HIF siRNA to RPE Cells RPE cells (ATCC, cell name: ARPE-19, catalog No.: CRL-2302) were seeded on a 96-well plate, and cultured to 30-50% cell density for transfection of siRNA. Then, siRNA and a transfection reagent (RNAi MAX, Invitrogen) were stirred in Opti-MEM (Invitrogen), and incubated for 20 min to give a siRNA-RNAi Max complex.

HIF siRNAs were the following products of Ambion (underlines show overhang consisting of deoxy form).

```
HIF-1α siRNA:
                                        (SEQ ID NO: 29)
sense-CCU CAG UGU GGG UAU AAG ATT, (SEQ ID NO: 30)
antisense-UCU UAU ACC CAC ACU GAG GTT, HIF-2α siRNA:
                                        (SEQ ID NO: 33)
sense-GGA CAU AGU AUC UUU GAC UTT,
and (SEQ ID NO: 34)
antisense-AGU CAA AGA UAC UAU GUC CTG
```

The medium was changed to a serum-free medium (DMEM medium or DMEM/F12 medium, Invitrogen), each siRNA was added to the RPE cells to a final concentration of 10 nM, and transfection was performed. Grouping was performed as follows.
(a) normoxia group
(b) hypoxia group
(c) hypoxia+drug group (HIF-1α siRNA 5 nM)
(d) hypoxia+drug group (HIF-2α siRNA 5 nM)
(e) hypoxia+drug group (HIF-1α siRNA 5 nM+HIF-2α siRNA 5 nM)
2) Culture of RPE Cells in Hypoxia System HIF siRNA was transfected into RPE cells, and subjected to hypoxic culture for 1 day using AnaeroPack for Cell (MITSUBISHI GAS CHEMICAL COMPANY, INC.) to induce VEGF expression. The cells cultured under normal oxygen concentration were used as a normoxia group.
3) RNA Extraction and Real-Time PCR After the completion of the hypoxia culture, total RNA was extracted with 50 μL of lysis solution (TaqMan Gene Expression Cell-to-CT kit, Applied Biosystems, catalog No.: AM1728) from the RPE cells. The extraction method followed the protocol of the explanatory leaflet attached to the TRIzol solution. Then, a reverse transcription reaction was performed using 1× RT buffer and 1× RT Enzyme Mix (contained in the aforementioned kit) and the obtained cDNA solution was subjected to a Real-time PCR reaction using TaqMan Gene Expression Master Mix (contained in the aforementioned kit). As the primer, a TaqMan Real-time PCR primer manufactured by Applied Biosystems (HIF-1α: Hs00153153 m1, HIF-2α: Hs01026142_m1, VEGF: Hs00173626 m1) was used.

2. Results and Discussion

Figure 4:
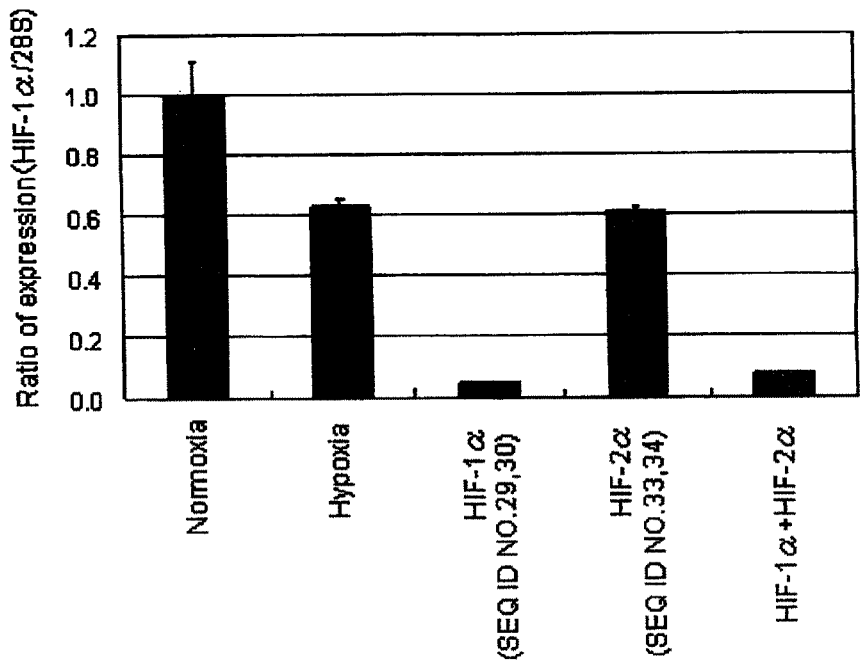
FIG. 4 is a graph showing the expression level of HIF-1α in RPE cells.
Figure 5:
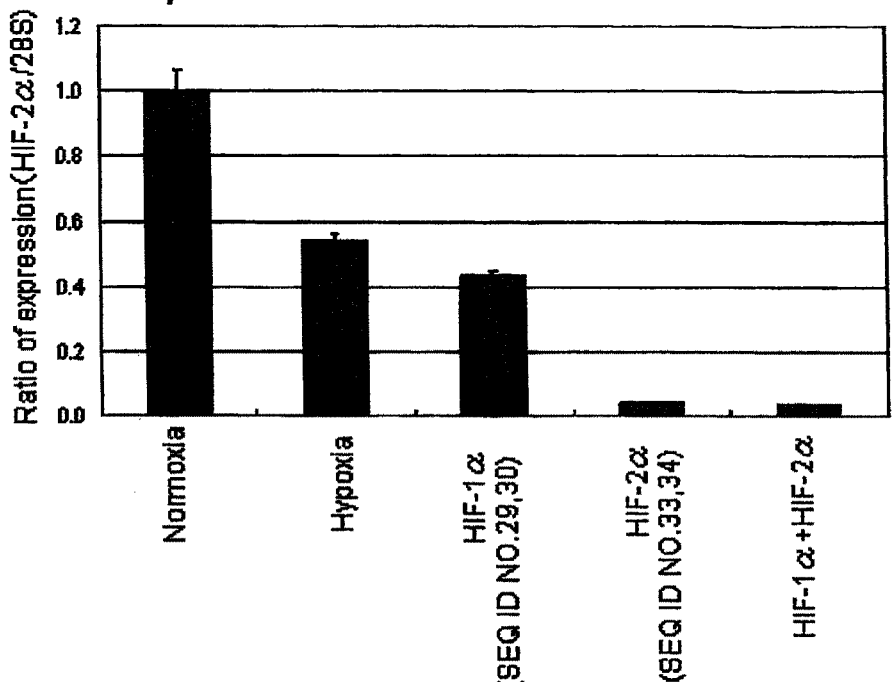
FIG. 5 is a graph showing the expression level of HIF-2α in RPE cells.
Figure 6:
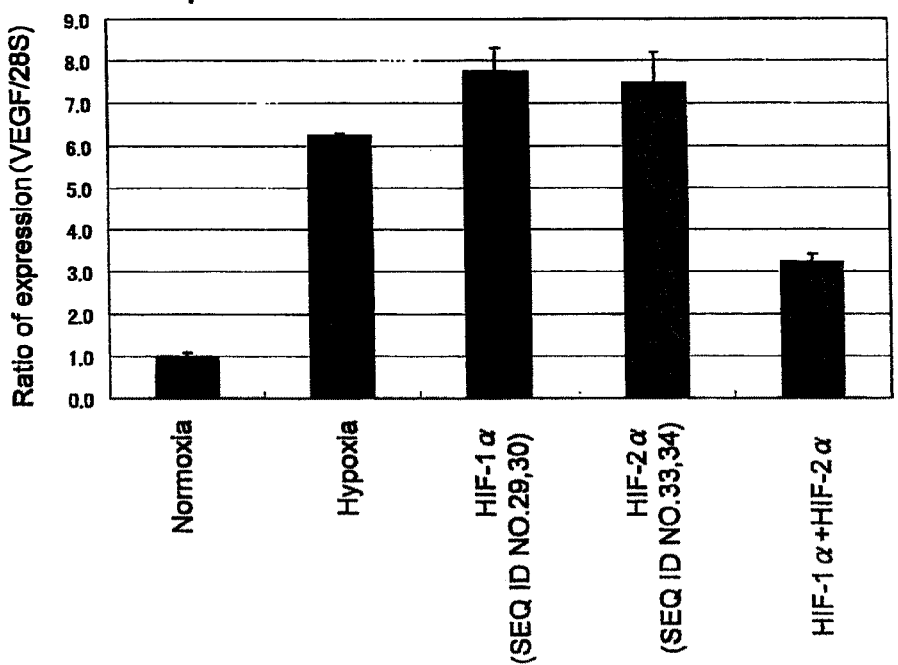
FIG. 6 is a graph showing the expression level of VEGF in RPE cells.

Whether addition of each of HIF-1α siRNA, HIF-2α siRNA and mixed siRNA of the both isoforms suppresses hyperexpression of VEGF due to a hypoxic treatment was examined using the RPE cells. FIG. 4 shows the expression level of HIF-1α. By the addition of HIF-1α siRNA alone or mixed siRNA consisting of the both isoforms, marked inhibition of HIF-1α expression was observed. On the other hand, FIG. 5 shows the expression level of HIF-2α, where the addition of HIF-2α siRNA alone, or mixed siRNA consisting of the both isoforms revealed inhibition of HIF-2α expression. Under the same conditions, suppression of VEGF expression was confirmed as shown in FIG. 6. A group supplemented with HIF-1α siRNA or HIF-2α siRNA alone did not show a VEGF expression suppressive effect. In contrast, a group supplemented with mixed siRNA consisting of the both isoforms showed a marked VEGF expression suppressive effect.

Experimental Example 3

Effect of HIF siRNA for VEGF Expression Induction in Retinal Pigment Epithelial (RPE) Cells 1. Method
1) Transfection of HIF siRNA to RPE Cells The experimental method followed Experimental Example 2 and an experiment was performed using the following siRNA of Amibon (underlines show overhang consisting of deoxy form).

```
HIF-1α siRNA:
                                   (SEQ ID NO: 8)
sense-gca cga cuu gau uuu cuc cTT, (SEQ ID NO: 14)
antisense-gga gaa aau caa guc gug cTT, HIF-2α siRNA:
                                   (SEQ ID NO: 10)
sense-ggu uuu guu g cu agc ccu uTT,
and
                                   (SEQ ID NO: 16)
antisense-aag ggc uag caa caa aac cTC
```

Figure 7:
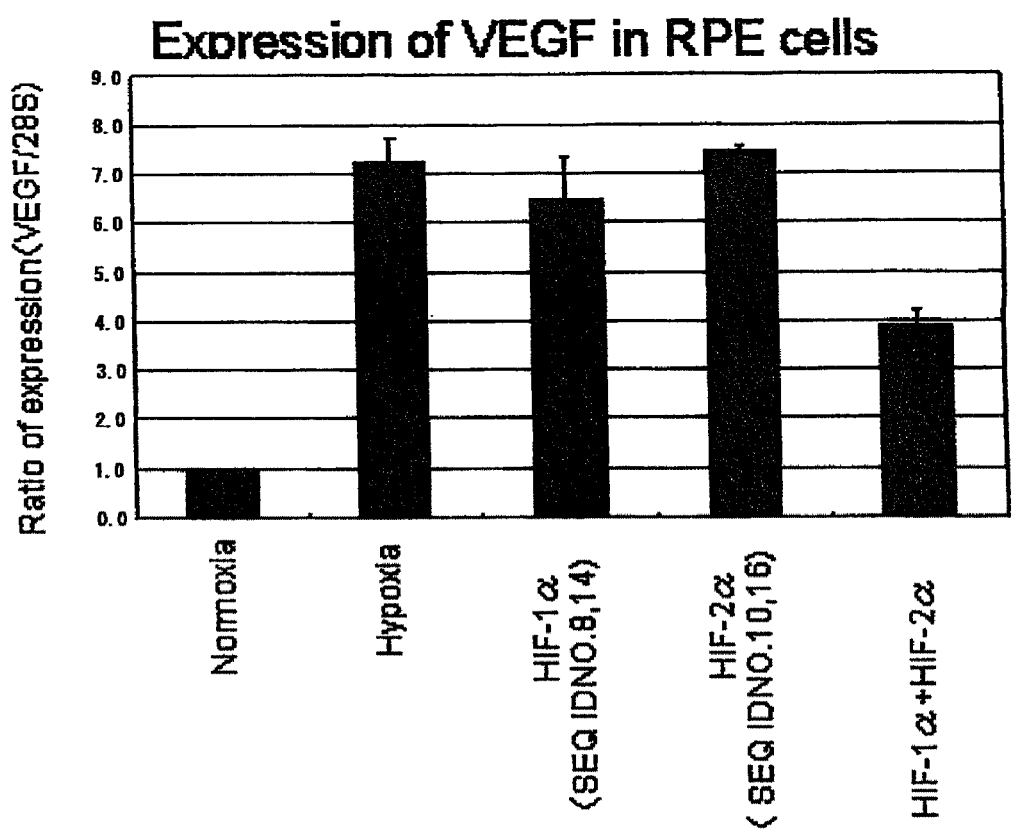
FIG. 7 is a graph showing the expression level of VEGF in RPE cells.

2. Results and Discussion:

As shown in FIG. 7, a group supplemented with HIF-1α siRNA or HIF-2α siRNA alone did not show a VEGF expression suppressive effect. In contrast, a group supplemented with mixed siRNA consisting of the both isoforms clearly showed a marked VEGF suppressive effect.

INDUSTRIAL APPLICABILITY

The therapeutic agent for a retinal disease of the present invention can effectively suppress VEGF production in the retinal cells, and is expected to afford a superior dose-effectiveness in the treatment of retinal diseases associated with angiogenesis, such as age-related macular degeneration, diabetic retinopathy and the like, as compared to conventional nucleic acid medicaments.

This application is based on a patent application No. 2007-204585 filed in Japan (filing date: Aug. 6, 2007), the contents of which are incorporated in full herein by this reference.

SEQUENCE LISTING FREE TEXT

SEQ ID NO: 5: sense strand of siRNA for human HIF-1α
SEQ ID NO: 6: sense strand of siRNA for human HIF-1α
SEQ ID NO: 7: sense strand of siRNA for human HIF-1α
SEQ ID NO: 8: sense strand of siRNA for human HIF-1α
SEQ ID NO: 9: sense strand of siRNA for human HIF-2α
SEQ ID NO: 10: sense strand of siRNA for human HIF-2α
SEQ ID NO: 11: antisense strand of siRNA for human HIF-1α
SEQ ID NO: 12: antisense strand of siRNA for human HIF-1α
SEQ ID NO: 13: antisense strand of siRNA for human HIF-1α
SEQ ID NO: 14: antisense strand of siRNA for human HIF-1α
SEQ ID NO: 15: antisense strand of siRNA for human HIF-2α
SEQ ID NO: 16: antisense strand of siRNA for human HIF-2α
SEQ ID NO: 17: sense strand of siRNA for human HIF-1α
SEQ ID NO: 18: sense strand of siRNA for human HIF-1α
SEQ ID NO: 19: sense strand of siRNA for human HIF-1α
SEQ ID NO: 20: sense strand of siRNA for human HIF-1α
SEQ ID NO: 21: sense strand of siRNA for human HIF-2α
SEQ ID NO: 22: sense strand of siRNA for human HIF-2α
SEQ ID NO: 23: antisense strand of siRNA for human HIF-1α
SEQ ID NO: 24: antisense strand of siRNA for human HIF-1α
SEQ ID NO: 25: antisense strand of siRNA for human HIF-1α
SEQ ID NO: 26: antisense strand of siRNA for human HIF-1α
SEQ ID NO: 27: antisense strand of siRNA for human HIF-2α
SEQ ID NO: 28: antisense strand of siRNA for human HIF-2α
SEQ ID NO: 29: sense strand of siRNA for human HIF-1α
SEQ ID NO: 30: antisense strand of siRNA for human HIF-1α
SEQ ID NO: 31: sense strand of siRNA for human HIF-1α
SEQ ID NO: 32: antisense strand of siRNA for human HIF-1α
SEQ ID NO: 33: sense strand of siRNA for human HIF-2α
SEQ ID NO: 34: antisense strand of siRNA for human HIF-2α
SEQ ID NO: 35: sense strand of siRNA for human HIF-2α
SEQ ID NO: 36: antisense strand of siRNA for human HIF-2α

The invention claimed is:

1. A method of treating a retinal disease associated with angiogenesis in a subject by inhibiting VEGF, the method comprising topically administering an effective amount of siRNA for HIF-1α and an effective amount of siRNA for HIF-2α to the eye of the subject, thereby inhibiting VEGF and treating the retinal disease associated with angiogenesis in the subject.

2. The method according to claim 1, wherein the aforementioned siRNA for HIF-1α consists of a sense strand comprising a sequence of 17-25 continuous bases of mRNA corresponding to the base sequence of SEQ ID NO: 1 and an antisense strand comprising a sequence complementary thereto, and the aforementioned siRNA for HIF-2α consists of a sense strand comprising a sequence of 17-25 continuous bases of mRNA corresponding to the base sequence of SEQ ID NO: 3 and an antisense strand comprising a sequence complementary thereto, and wherein the sense strand and antisense strand are 17-25 bases in length.

3. The method according to claim 1, wherein the aforementioned siRNA for HIF-1α is the following (a) or (b), and siRNA for HIF-2α is the following (c) or (d):

(a) a double strand RNA composed of a sense strand comprising a base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;

(b) a double strand RNA composed of a sense strand comprising a base sequence wherein one to several bases have been added to and/or deleted from the 5' terminal and/or 3' terminal of the base sequence described in any of SEQ ID NOs: 17-20 and 31, and an antisense strand comprising a sequence complementary thereto, which optionally has an overhang at the terminal of the sense strand and/or the antisense strand, and has HIF-1α expression-inhibitory activity;

(c) a double strand RNA composed of a sense strand comprising the base sequence described in any of SEQ ID NO: 21, 22 and 35, and an antisense strand comprising a sequence complementary thereto, which optionally has an overhang at the terminal of the sense strand and/or the antisense strand, and has HIF-2α expression-inhibitory activity;

(d) a double strand RNA composed of a sense strand comprising a base sequence wherein one to several bases have been added to and/or deleted from the 5' terminal and/or 3' terminal of the base sequence described in any of SEQ ID NOs: 21, 22 and 35, and an antisense strand comprising a sequence complementary thereto, which optionally has an overhang at the terminal of the sense strand and/or the antisense strand, and has HIF-2α expression-inhibitory activity.

4. The method according to claim 1, wherein the aforementioned siRNA for HIF-1α is any of the following (1-1)-(1-5), and siRNA for HIF-2α is any of the following (2-1)-(2-3):

(1-1) a double strand RNA composed of a sense strand consisting of the base sequence described in SEQ ID NO: 5, and an antisense strand consisting of the base sequence described in SEQ ID NO: 11;

(1-2) a double strand RNA composed of a sense strand consisting of the base sequence described in SEQ ID NO: 6, and an antisense strand consisting of the base sequence described in SEQ ID NO: 12;

(1-3) a double strand RNA composed of a sense strand consisting of the base sequence described in SEQ ID NO: 7, and an antisense strand consisting of the base sequence described in SEQ ID NO: 13;

(1-4) a double strand RNA composed of a sense strand consisting of the base sequence described in SEQ ID NO: 8, and an antisense strand consisting of the base sequence described in SEQ ID NO: 14;

(1-5) a double strand RNA composed of a sense strand consisting of the base sequence described in SEQ ID NO: 29, and an antisense strand consisting of the base sequence described in SEQ ID NO: 30;

(2-1) a double strand RNA composed of a sense strand consisting of the base sequence described in SEQ ID NO: 9, and an antisense strand consisting of the base sequence described in SEQ ID NO: 15;

(2-2) a double strand RNA composed of a sense strand consisting of the base sequence described in SEQ ID NO: 10, and an antisense strand consisting of the base sequence described in SEQ ID NO: 16;

(2-3) a double strand RNA composed of a sense strand consisting of the base sequence described in SEQ ID NO: 33, and an antisense strand consisting of the base sequence described in SEQ ID NO: 34.

5. The method according to claim 1, wherein the retinal disease associated with angiogenesis is age-related macular degeneration, diabetic retinopathy, retinopathy of prematurity, retinal vein occlusion, retinal artery obstruction, diabetic macular edema or glaucoma.

6. The method according to claim 5, wherein the retinal disease associated with angiogenesis is age-related macular degeneration or diabetic retinopathy.

* * * * *